United States Patent
Coffey et al.

(10) Patent No.: US 10,610,349 B2
(45) Date of Patent: Apr. 7, 2020

(54) DEVICE FOR DEPLOYING A FLEXIBLE IMPLANT

(75) Inventors: Peter Coffey, London (GB); Lyndon Da Cruz, London (GB); Karen Cheetham, Borehamwood (GB)

(73) Assignee: UCL BUSINESS LTD, London (GB)

(*) Notice: Subject to any disclaimer, the term of this patent is extended or adjusted under 35 U.S.C. 154(b) by 1042 days.

(21) Appl. No.: 13/808,486

(22) PCT Filed: Jul. 5, 2011

(86) PCT No.: PCT/GB2011/051262
§ 371 (c)(1),
(2), (4) Date: May 6, 2013

(87) PCT Pub. No.: WO2012/004592
PCT Pub. Date: Jan. 12, 2012

(65) Prior Publication Data
US 2013/0218167 A1    Aug. 22, 2013

(30) Foreign Application Priority Data

Jul. 5, 2010   (GB) .................................. 1011313.2

(51) Int. Cl.
*A61F 2/14* (2006.01)
*A61F 9/007* (2006.01)
(Continued)

(52) U.S. Cl.
CPC ................ *A61F 2/14* (2013.01); *A61F 9/007* (2013.01); *A61F 9/0017* (2013.01); *A61K 9/0051* (2013.01)

(58) Field of Classification Search
CPC ...... A61F 2/1662; A61F 2/1667; A61F 2/167; A61F 2/1672; A61F 2/14; A61F 2/148;
(Continued)

(56) References Cited

U.S. PATENT DOCUMENTS 4,240,163 A * 12/1980 Galin .................... A61F 2/1613
                                                   424/427
4,699,140 A * 10/1987 Holmes ................. A61F 2/1662
                                                   606/107
(Continued)

FOREIGN PATENT DOCUMENTS

CA    2927921 A1    8/2007
DE    3610925 A1   10/1987
(Continued)

OTHER PUBLICATIONS

International Serach Report for PCT/GB2011/051262 dated Oct. 18, 2011.
(Continued)

*Primary Examiner* — Tan-Uyen T Ho
*Assistant Examiner* — Chima U Igboko
(74) *Attorney, Agent, or Firm* — Banner & Witcoff, Ltd.

(57) ABSTRACT

The invention relates to devices and methods for deploying an implant. Preferably the device (10) deploys a flexible implant in an eye. In one embodiment, the device comprises a distal end and a proximal end, wherein the distal end is constructed and arranged to cause said implant to be flexed into a curved configuration when in a carried position and the device is configured to urge said flexed implant from said carried position to a deployed position. Embodiments with removable tips (13) and wheel actuators (14) are also disclosed.

17 Claims, 24 Drawing Sheets

(51) Int. Cl.
*A61F 9/00* (2006.01)
*A61K 9/00* (2006.01)

(58) Field of Classification Search
CPC ........ A61B 2017/0409; A61B 17/0057; A61B 2017/00623; A61K 9/0051
USPC .......................................................... 606/107
See application file for complete search history.

(56) References Cited

U.S. PATENT DOCUMENTS

| | | | |
|---|---|---|---|
| 4,836,201 A | | 6/1989 | Patton et al. |
| 5,817,075 A | * | 10/1998 | Giungo .................. A61B 90/00 |
| | | | 600/567 |
| 6,228,094 B1 | | 5/2001 | Erdman |
| 6,976,989 B1 | | 12/2005 | Vincent |
| 8,029,515 B2 | * | 10/2011 | Shiuey .................... A61F 2/142 |
| | | | 606/107 |
| 8,439,898 B2 | * | 5/2013 | Lam ....................... A61B 1/018 |
| | | | 606/1 |
| 2001/0014808 A1 | | 8/2001 | Kikuchi et al. |
| 2003/0050646 A1 | * | 3/2003 | Kikuchi ................ A61F 2/1678 |
| | | | 606/107 |
| 2006/0106401 A1 | | 5/2006 | Deutschmann et al. |
| 2006/0229634 A1 | | 10/2006 | Shepherd |
| 2006/0235430 A1 | | 10/2006 | Le et al. |
| 2009/0112223 A1 | | 4/2009 | Downer et al. |
| 2009/0292293 A1 | * | 11/2009 | Bogaert ................ A61F 2/1664 |
| | | | 606/107 |
| 2010/0030246 A1 | * | 2/2010 | Pavcnik ............. A61B 17/0057 |
| | | | 606/157 |
| 2010/0114151 A1 | * | 5/2010 | Mujwid ........... A61B 17/12172 |
| | | | 606/194 |
| 2011/0009874 A1 | * | 1/2011 | Wardle ................ A61F 9/00781 |
| | | | 606/108 |

FOREIGN PATENT DOCUMENTS

| | | |
|---|---|---|
| EP | 0363213 A2 | 4/1990 |
| EP | 0544948 A1 | 6/1993 |
| EP | 1262154 A1 | 12/2002 |
| EP | 2177178 A1 | 4/2010 |
| WO | 2007132332 A2 | 11/2007 |
| WO | 2008098187 A2 | 8/2008 |
| WO | 2008121649 A1 | 10/2008 |
| WO | 2009154187 A1 | 12/2009 |
| WO | 2010017933 A1 | 2/2010 |
| WO | 2010064275 A1 | 6/2010 |
| WO | 2011006078 A1 | 1/2011 |

OTHER PUBLICATIONS

Office Action issued in related Japanese Application No. 2013-517545 dated Nov. 24, 2015.
Search Report issued in related Great Britain Application No. 1011313.2, dated Sep. 29, 2010.
Search Report which searched claims 22-33, 37 and 44 issued in related Great Britain Application No. 1011313.2, dated Feb. 28, 2011.
Search Report which searched claims 10-21, 22-33, 37 and 44 issued in related Great Britain Application No. 1011313.2, dated Feb. 28, 2011.
Dec. 4, 2018 (CA) Office Action—App 2,804,078.
May 21, 2019—(IN) Examination Report—App 11191/DELNP/2012.

* cited by examiner

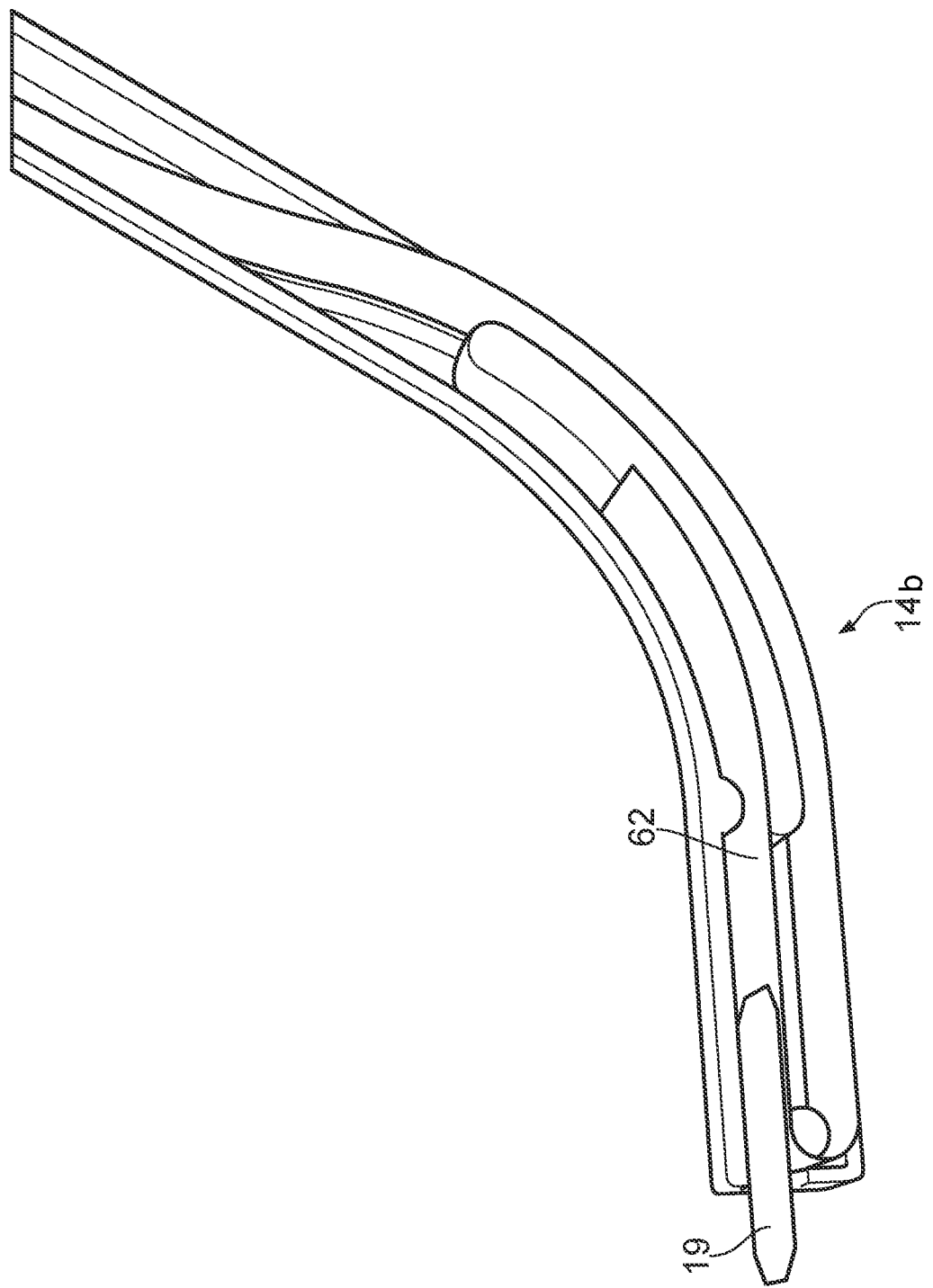

DEVICE FOR DEPLOYING A FLEXIBLE IMPLANT

This invention relates to devices and methods for deploying an implant. The devices and methods allow for simple, reliable and efficient deployment of an implant. Preferably, the device is for deploying an implant anywhere in an eye, with particular application to deploying implants into the sub-retinal space or vitreous chamber. The invention also relates to the implants themselves.

Damage to the retina in the back of the eye and, more specifically, damage to the sub retinal space under the retina can cause an impairment of vision and/or blindness. A common cause of blindness is macula degeneration. The macula is located in the back of the eye in the central portion of the retina and is responsible for central vision. It may be possible to help prevent macula degeneration and any other diseases or abnormalities in the eye by providing stem cells to help regenerate or cure that part of the eye. However, surgical correction of diseases or abnormalities in the eye and especially at the back of the eye is extremely difficult and awkward. Furthermore, the tissues around the eye are very fragile, thus any misplaced movement or contact can damage the eye. There are at present very few commercially available devices that are capable of delivering implants to an eye.

WO 98/22029 discloses an instrument for implanting retinal tissue into the sub-retinal space of the eye. The device operates by moving a mandrel through the inside of a nozzle to push a piece of retinal tissue out of the nozzle exit. In this device, the retinal tissue is carried in a substantially flat configuration and the mandrel has the same cross-sectional shape as the retinal issue and the internal nozzle. Accordingly, the incision made in the eye to accept the instrument must be the same width as the retinal tissue being implanted. Furthermore, because the retinal tissue is carried and deployed in a flat configuration, it can crumple or buckle under the force applied from the mandrel.

The present invention provides new devices and methods for simple and easy deployment of implants, particularly into the eye.

According to a first aspect of the invention, there is provided a device for deploying a flexible implant, the device comprising: a distal end; and a proximal end, wherein the distal end is constructed and arranged to cause the implant to be flexed into a curved configuration when in a carried position; and the device is configured to urge the flexed implant from the carried position to a deployed position.

This aspect of the invention allows for an implant to be deployed into an eye, while minimising the size of the incision required to insert the implant into the eye. As the implant is curved in the carried position, the width of the incision can be reduced. When the implant is in the deployed position, the implant can preferably unfurl and flatten. Thus it is possible to deploy an implant with a large width while providing a small incision in the eye. Further, as the implant is flexed into a curved configuration in the carried position by the distal end, the implant can exert a force on the device, thereby allowing it to be secured more firmly to the distal end while being carried. This also allows the implant to be secured to the device in a way such that only one surface of the implant may contact the device. This further increases the reliability of the implant as the surface that contains the active agent or medicament (such as stem cells) is not disrupted when the implant is in the carried position or during deployment. An additional effect of the curved configuration is that the implant becomes resistant to buckling or creasing during deployment, allowing it to be pushed out of the device, even though the implant is made form flexible material.

The distal end of the device according to the first aspect may further be arranged so that, as the implant is inserted into the device, the distal end causes the implant to flex into the curved configuration. This allows easy loading of the implant, without a need to pre-curl the implant before presenting it to the device.

The distal end is preferably arranged so that it only contacts one surface (preferably the one that does not contain the medicament) of the implant during insertion. Thus there is minimal contact with the surface that contains the medicament. This allows for a more reliable implant as there is less chance of interference or contamination of the surface containing the medicament.

Preferably the distal end of the above devices may also be arranged so that, as the implant is urged from the carried position to the deployed position, the implant flattens. This allows the implant to be deployed and flattened in a single movement, thus providing simple and efficient deployment. The flattening is preferably achieved by the inherent nature of the implant providing a restoring force to a flat configuration.

According to a second aspect of the invention, there is provided a device for deploying a flexible implant, the device comprising: a distal end; and a proximal end, wherein: the distal end is constructed and arranged to cause the implant to be flexed into a curved configuration when in a carried position; and the distal end is constructed and arranged such that, as the implant is inserted into the distal end of the device, the distal end causes the implant to flex into the curved configuration.

The distal end preferably curves the implant while it is being inserted into the device. Thus there is no need to apply any additional force on the implant to curve it. This allows simple insertion of the implant into the device and, as no force has to be applied to the medicament surface of the implant, provides a more reliable implant.

The simplicity of the insertion and deployment of the implant allows the device to be compact, thus reducing the size of the incision required to be made to the eye.

Preferably, the distal end of the devices described above may comprise an opening through which the implant is inserted into, and deployed from, the device. More preferably, the opening may be angled away from a plane perpendicular to the direction of insertion and/or deployment of the implant. Preferably the angle is between 10° and 80°, compared to that plane, more preferably between 20° and 70°, especially between 30° and 60°. The angled opening provides an efficient and effective way of curving the implant during insertion. It may also help to flatten the implant during deployment. Shaping the device in this way also helps to minimise any interference between the device and the surface of the implant carrying the medicament. The angled opening also allows the device to be more easily introduced into through the sclera and retina, a smaller slit opening in the eye being required than if the tip opening were parallel to the plane perpendicular to the plane of insertion.

Preferably, the proximal end of any of the devices described above may comprise an actuator, that, when actuated, causes the device to urge the flexed implant from the carried position to the deployed position. The actuator may be arranged to be depressed, to slide or to rotate, for example, in order to cause movement, especially linear movement of the implant. More preferably, the actuator is arranged to rotate, wherein rotational movement of the actuator causes linear movement of the implant. This allows quick, easy and intuitive deployment of the implant, by a simple operation carried out at the proximal end of the device. The rotational movement may be obtained by turning a wheel, either towards or away from the implant.

According to a third aspect of the invention there is provided a device for deploying a flexible implant, the device comprising: a distal end; and a proximal end, wherein the proximal end comprises an actuator, the actuator being arranged to rotate, wherein rotational movement of the actuator causes linear movement of the implant.

An actuator that rotates allows the user to make simple and easy movements to actuate the device. The easier movements allows the user to smoothly rotate the actuator, and such smooth rotation provides a smoothly applied force for deployment of the implant. This helps prevent the implant deforming due to inconsistencies in the applied force, such as sudden increases in the force applied.

Preferably, in the devices described above the actuator can be a wheel. A wheel can be easily rotated by a user. This provides greater control when deploying the implant.

The devices described above may be constructed and arranged to urge the implant in a direction generally transverse to the direction in which the implant is curved when in the curved configuration at the carried position.

When urging the implant a force can be applied to an edge of the curved implant in a direction that is transverse to the direction in which the implant is curved. A greater force can be applied to the curved implant in this direction as the curvature helps resist deformation of the implant in the direction transverse to the direction of the applied force.

The devices described above may be arranged so that the implant may be urged from the carried position to a deployed position by an urging member. The urging member helps convey a force from the proximal end of the device to the distal end of the device where the implant is carried and deployed from. This allows the device to be long and thin so that one end of the device can be easily inserted into the eye. The urging member is preferably elongate and may be flexible. It can be embodied by a wire, suture or other suitable means. Whilst in most embodiments the urging member is solid, it could in other embodiments by a hydraulic piston, such as a column of fluid, used to drive a solid urging portion which contacts the implant to urge it from the device.

Preferably, the urging member is arranged to contact a part of an edge of the implant and this is preferably done when it is in its curved configuration. In particular, the urging member is preferably arranged such that when the implant and urging member are in contact the implant edge is positioned substantially across the midline of the end of the urging member. This allows the urging member to urge the implant from the device whilst reducing the likelihood of the urging member passing over or under the implant. Correct positioning of the urging member and the implant may be achieved by appropriate shaping of the tip region to locate the implant and urging member in relation to each other.

When the implant is in a curved configuration, the implant is more rigid. Therefore, when the urging member applies a force to a part of the edge of the implant, the implant does not crumple as the curvature of the implant helps provide greater structural stability along the direction that the force is applied. Thus the device allows the implant to be more effective and reliable.

Preferably, the actuator may be connected to the urging member so that actuation of the actuator causes the urging member to urge the implant from the carried position to the deployed position. More preferably, the urging member is elongated along a longitudinal direction. The urging member may be a wire, a coiled wire or a suture. This allows the actuating force applied at the proximal end of the device to be conveyed to the distal end of the device, which can be inserted into the eye. This allows the distal end to be compact and small, thus being easily insertable into the eye.

In order to limit the movement of the urging member, to prevent it being retracted too far within the device, or extended out of the device, the device may be provided with one or more limiting members. Said limiting members may be provided on the urging member, as part of the actuating member or separately from either, but arranged to interact with one or both of the urging member and the actuating member. For example, the device may be provided with a back-stop to prevent excessive retraction of the urging member.

In the devices of the invention, the distal end may be arranged to guide the urging member so that the implant moves from the carried position to the deployed position. Preferably, the device comprises a guiding means that is arranged to guide the urging member. The guiding means is usefully configured to not completely surround the urging member, and may be embodied as a groove. This allows the urging member to follow the guiding means even at positions formerly occupied by the implant, without any need for there to be any contact with the top surface of the implant.

Preferably, the guiding means is located underneath the implant when the implant is in the carried position.

The guiding means can be configured by lips that guide either side of the urging member.

According to a fourth aspect of the invention, there is provided a device for deploying a flexible implant, the device comprising: a distal end; a proximal end; an urging member for urging the implant from a carried position to a deployed position; and a guiding means arranged to guide the urging member in a direction in which the implant is moved from the carried position to the deployed position and to restrain movement of the urging member in a direction that is perpendicular to this direction.

This allows the urging member to move in a fixed direction, which includes the direction of deployment. This provides a more reliable deployment of the implant as the urging member cannot easily deviate from the path required to deploy the implant.

Furthermore, the guiding means may allow the urging member to move in a direction that is perpendicular to the edge of the implant that the urging member contacts. Thus, the urging member can be positioned such that the amount of area of the edge of the implant that the urging member contacts is increased. This helps to prevent the urging member slipping above the edge of the implant and therefore helps to provide more reliable deployment of the implant. This also helps to stop the urging member from contacting the surface of the implant that carries the medicament.

In the devices of the invention, the guiding means may comprise a groove. The groove may have protruded lips either side of it, at least at the distal end of the groove.

In the devices of the invention, the distal end may be arranged so that, when the implant is in the carried position, the device contacts substantially a single surface of the implant to secure the implant to the device. The distal end may be further arranged so that a surface of the implant does not contact the device. This provides a more effective implant as the surface that contains the medicament is not interfered with. Thus the surface can be kept clean, sterile and undisturbed. This helps improve the reliability of the implant.

In the devices described, the distal end may comprise curved interior walls. The interior cross-section is preferably non-circular, so as to allow a planar implant to be carried. The curved walls may be curved within a plane that is perpendicular to the longitudinal axis of the distal end. Furthermore, the curvature of the walls may increase such that, when the implant is in the carried position or when the implant is urged from the carried position to the deployed position, the walls restrict movement of the implant in a direction generally transverse the direction the implant is deployed. This allows the implant to be effectively secured inside the device while keeping a surface of the implant from contacting the device. The curved walls also provide protection for the implant from outside objects, especially during incision of the device in to the eye, thus increasing reliability of the implant.

In the devices of the invention, the walls can be arranged to guide the urging member. This helps improve the reliability of deployment of the implant.

The device may be arranged such that a longitudinal axis of the proximal end has a direction that is different to a direction in which the implant is deployed. The angle at which the implant is required to be deployed may be different to the angle at which the device is inserted into the eye, due to the geometry of the eye. Thus helps provide easier deployment of an implant in the eye.

The distal end of the device may comprise a tip that may be removably attachable to the proximal end. The proximal end may comprise a handle. A removably attachable tip that is disposable may be desirable for the purposes of hygiene. This device is also cost efficient as the handle can be re-used. As an alternative, the whole device may be disposable.

The implant used in the devices described above can be flexible, substantially planar, substantially flat and can preferably comprise stem cells. Alternatively or additionally, the surface can be drug-eluting or may comprise radioactive material. The flexibility of the implant allows it to be carried in a curved configuration, the benefits of which are described above. Additionally, as the implant is flexible, when the implant is in a deployed position, the implant can conform to the shape of the surface on which it has been deployed (such as the eye). Furthermore, providing a substantially flat implant allows easy deposition or incorporation of the medicament onto or into one or more surfaces of the implant, or within the implant.

The implant may be inserted into any of the heredescribed devices in a way that the leading edge of the implant contacts the angled opening described above, the contact causing the implant to flex into the curved configuration. An edge of the planar implant contacts the angled opening when inserted into the device. The angled opening will initially contact the edge of the implant at two points situated away from each other. This can cause the planar implant to bend in the middle as it is being inserted. This provides an effective method of curving the implant simply by pushing the implant into the device. There is no need to pre-curl or otherwise contact the surface of the implant that carries the medicament.

Stem cells may be provided on a surface of the implant and the surface preferably does not contact any part of the device when the implant is carried in the device or while the implant is urged from the carried position to the deployed position. This helps improve the reliability and effectiveness of the implant.

Any of the heredescribed implants may be used in any of the heredescribed devices.

According to another aspect of the invention, there is provided a method of deploying a flexible implant in an eye, comprising the steps of: carrying the implant, the implant being in a curved configuration whilst carried; and deploying the carried implant.

The implant may preferably flatten after deployment.

According to another aspect of the invention, there is provided a method of deploying a flexible implant, the method comprising the steps of inserting the implant into a device, wherein as the implant is inserted into the device, the implant is caused to assume a curved configuration; and deploying the implant out of the device.

As the implant leaves the device, the implant can flatten.

According to another aspect of the invention, there is provided a method of deploying a flexible implant, comprising the step of rotating an actuating means, wherein rotational movement of the actuating means causes linear movement of the implant.

According to another aspect of the invention, there is provided a method of deploying a flexible implant, the method comprising the step of urging, by using an urging member, the implant from a carried position to a deployed position; during the urging, guiding the urging member in a direction in which the implant is moved from the carried position to the deployed position and in a direction that is perpendicular to the direction.

According to another aspect of the invention, there is provided a device as previously described, further comprising an implant comprising a membrane and a layer of cells. The membrane is preferably non-biodegradable and porous. The cells are preferably retinal derivative cells, especially retinal pigmented epithelial cells.

Any number of the features of the various aspects of the inventions may be combined in any embodiment.

The invention will be further described below, by way of non-limitative example only, with reference to the accompanying drawings, in which:

FIGS. 15A and 15B show a sixth embodiment of the device;

FIG. 1 depicts a first embodiment of a device 10 according to the invention that can be used to implant or deploy an implant or other object, preferably directly into an eye. The device 10 may be used to deploy an implant anywhere in the eye, for example, in the vitreous chamber or in the subretinal space of an eye.

The device preferably has a means for a user to grip the device, for example a handle 11. The handle is generally located at the proximal end of the device (as seen from the user's point of view). The handle may be made from stainless steel (e.g. stainless steel 316) or medical grade plastic. The handle can conveniently be provided in two mirror image parts 11a and 11b, with the split being along the longitudinal axis of the handle 11. Any fasteners used to assemble the handle can by usefully made from A4 stainless steel.

Figure 1:
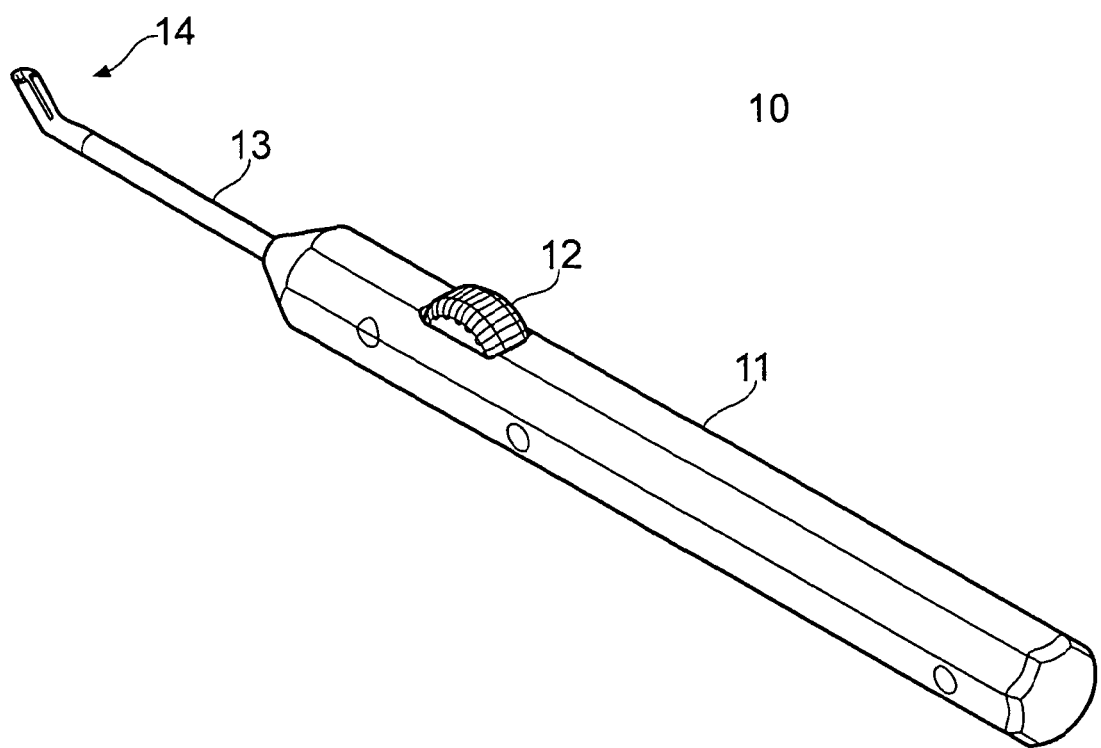
FIG. 1 shows a first embodiment of a device in accordance with the present invention.

Preferably, the handle 11 is shaped so as to provide a secure grip for a user of the device 10 and so that the device can be easily gripped. This may help provide greater control and prevent damage to the eye during surgery due to slippage of the device 10. As shown in FIG. 1, the handle 11 may be shaped to have a polyhedron cross section, so that the faces and edges can help provide increased grip. In FIG. 1, the handle has a generally octagonal cross-sectional shape, although any suitable shape may be used, such as hexagonal, square or circular.

The device may also include a user-actuatable actuator for actuating the device 10. The actuator may be placed on or partially within the handle 11. In the first embodiment, the actuator can be a wheel 12. The wheel 12 is rotated by the user to actuate the device 10. The actuator can be configured so that actuation can occur when the wheel is rotated in the clockwise direction or the actuator can be configured so that actuation can occur when the wheel is rotated in the anti-clockwise direction. In the FIG. 1 embodiment (see also FIGS. 8 and 9), movement of the wheel generally towards the user causes the implant to move from the carried position to the deployed position. The wheel 12 may comprise ridges to help increase grip during rotation.

Figure 15A:
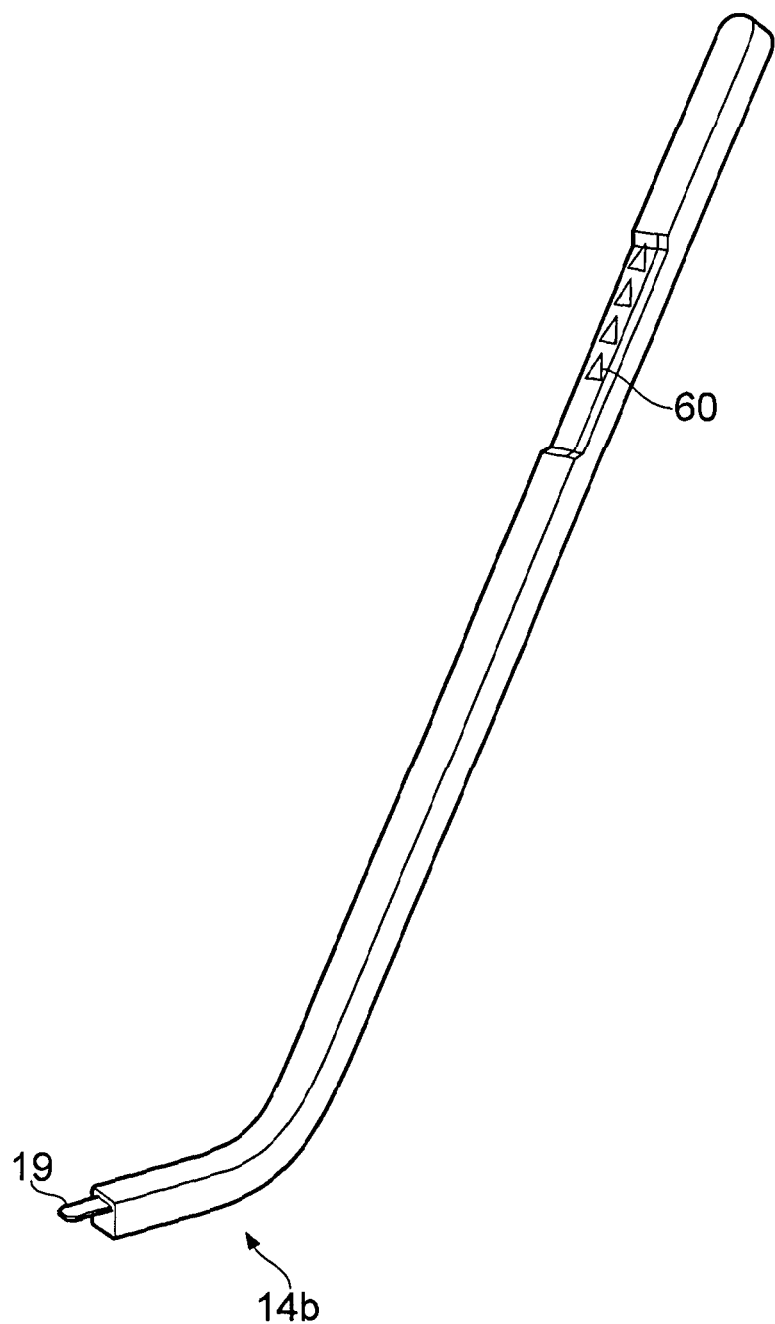
Figure 16A:
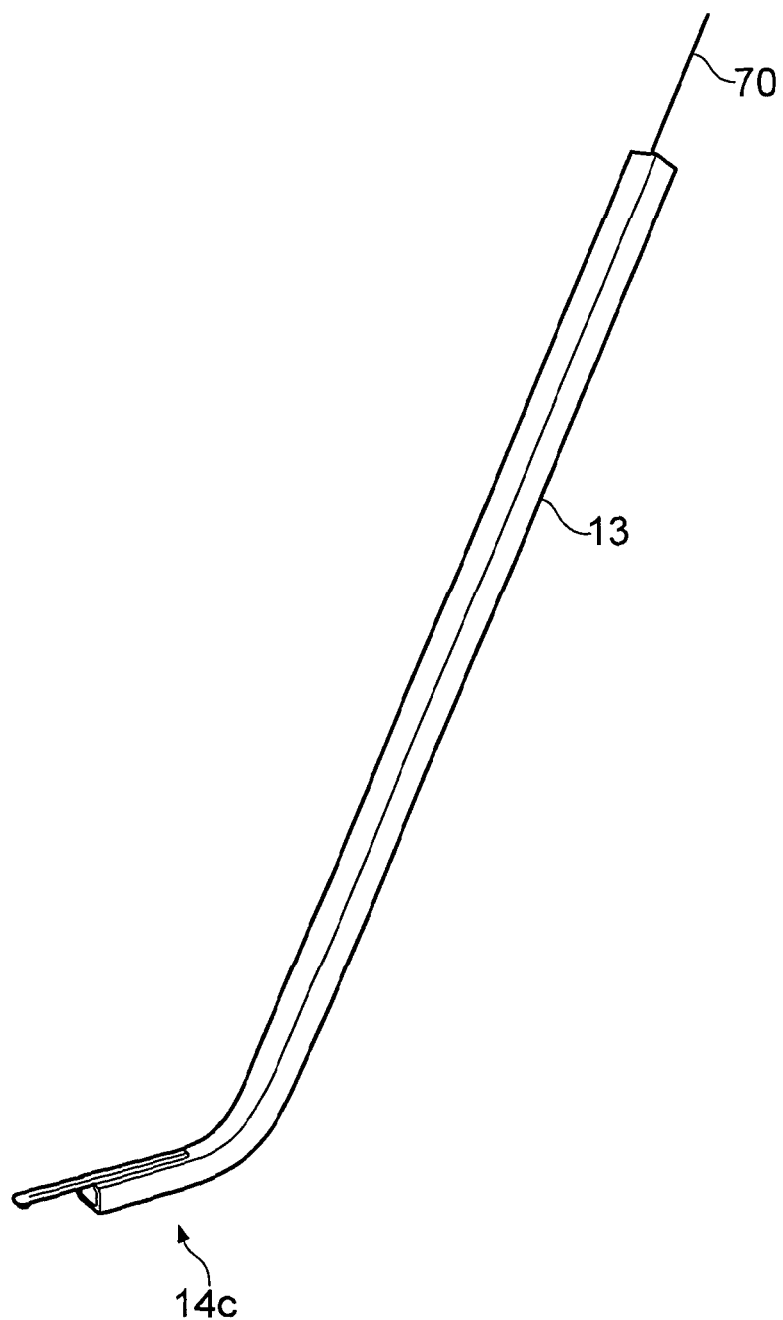
FIGS. 16A and 16B show a seventh embodiment of the device.
Figure 16B:
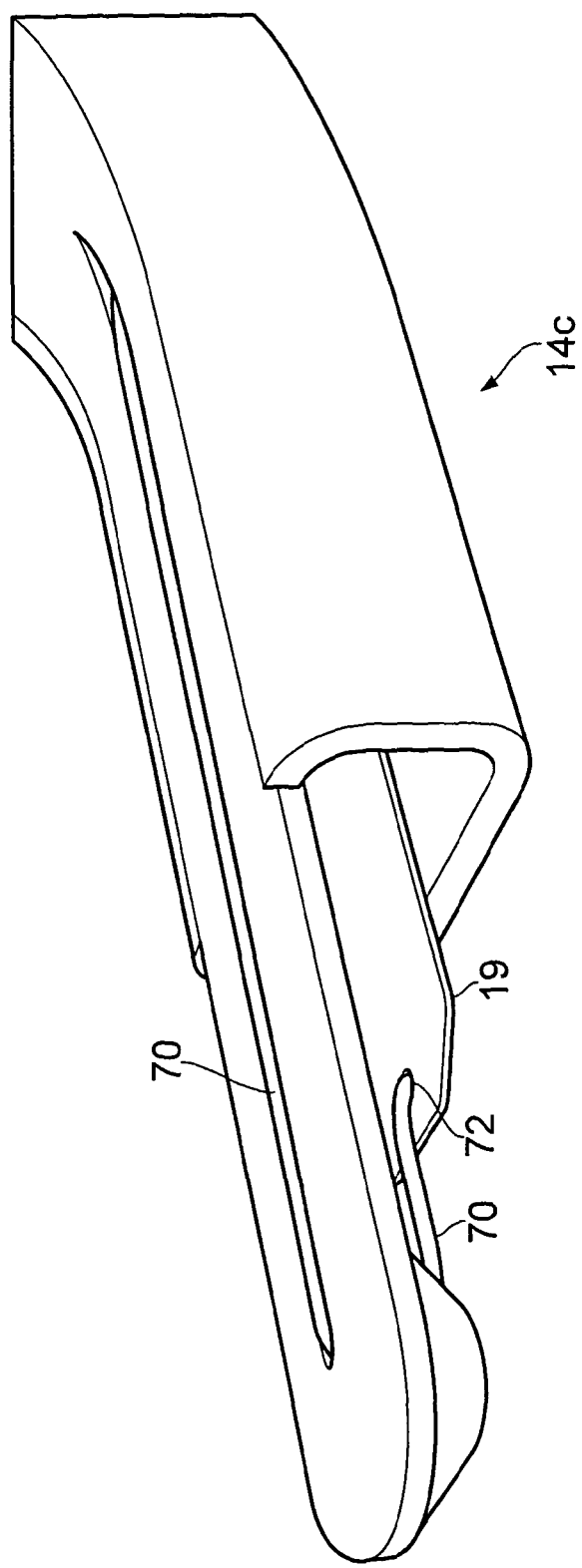
Figure 17A:
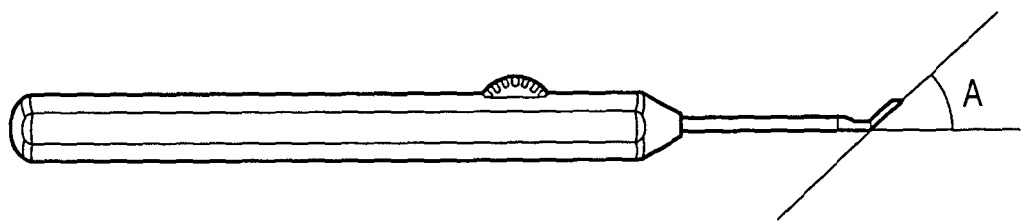
FIGS. 17A and 17B show a side view of one embodiment of the device.
Figure 17B:
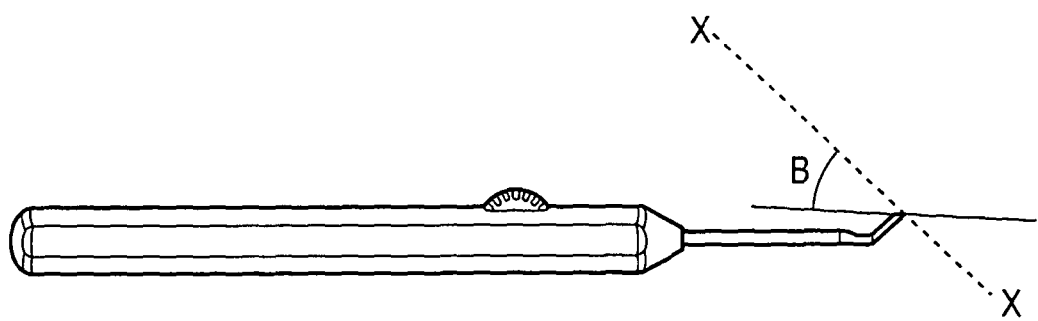

The actuator is not limited to a wheel. For example, the actuator may be a string (for example as shown in the embodiment of FIGS. 16A and 16B), a plunger, a switch (that, for example, actuates a motor), a lever, a roller, a slider, a conveyer belt (for example as shown in the embodiment of FIGS. 15A and 15B) or such like.

The device 10 may include a tip portion 13 at its distal end. The tip portion 13 may be removably attachable to the handle 11. The device may alternatively be a single continuous piece with an integrated handle and tip portion. The tip portion 13 may be made from plastic or a metal such as stainless steel or gold. Stainless steel 316L is preferred for the tip portion.

Figure 8:
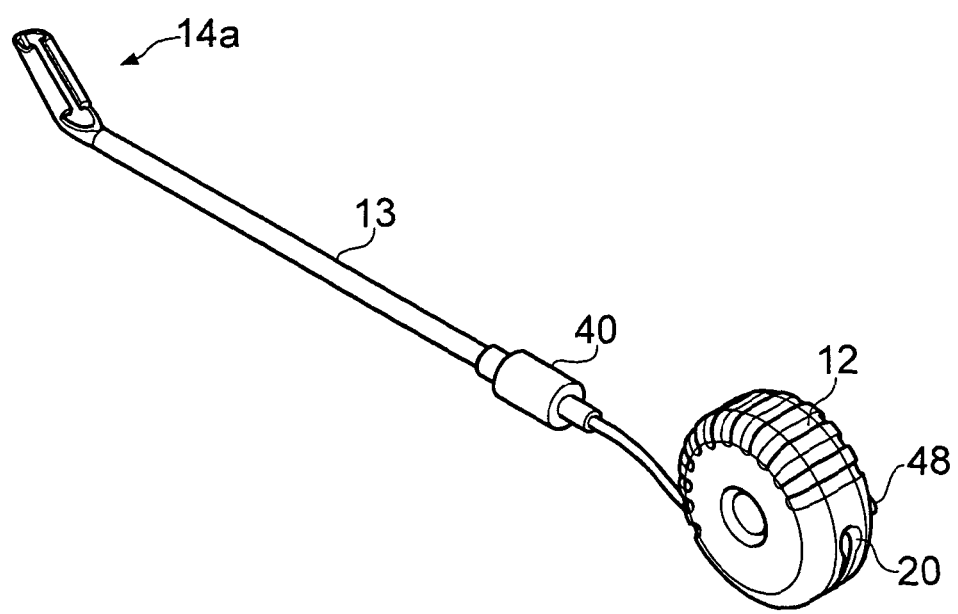
FIG. 8 shows the connection of an actuator wheel to an urging member.
Figure 9:
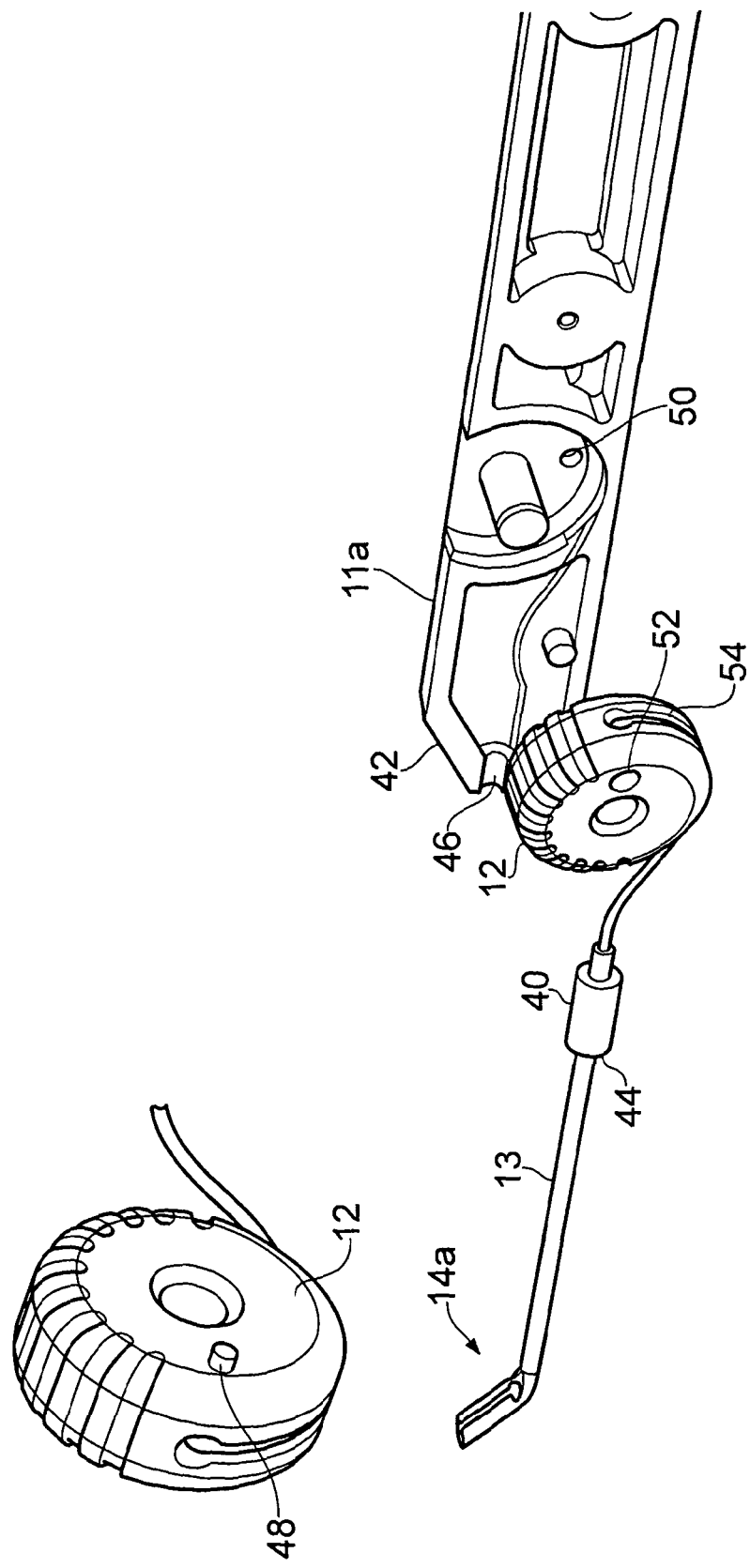
FIG. 9 shows how the mechanism of FIG. 8 fits inside a handle component.

The tip portion 13 preferably extends some distance inside the handle 11 when the device is assembled (see FIG. 9). A proper fit of the tip portion 13 in the handle can be achieved by providing an annulus of flexible silicon 40 (see FIGS. 8 and 9) around the outside of the proximal end of the tip portion 13, and by clamping this silicon within a chamber 42 inside the handle. The flexible silicon 40 is preferably slightly larger than the internal dimensions of the chamber 42, so as to provide a tight clamping fit when the handle halves 11a, 11b are tightened together. The tip portion 13 may also be provided with a suitable flange portion 44, that interacts with a corresponding flange portion 46 inside the handle 11 to prevent the tip 13 from coming out of the handle 11 during use.

The distal end of the tip portion 13 may comprise the head portion 14. The proximal end of the device may comprise the handle 11 only or the handle 11 and the elongated and narrow part of the tip portion (i.e. the tip portion not including the head portion).

Figure 2:
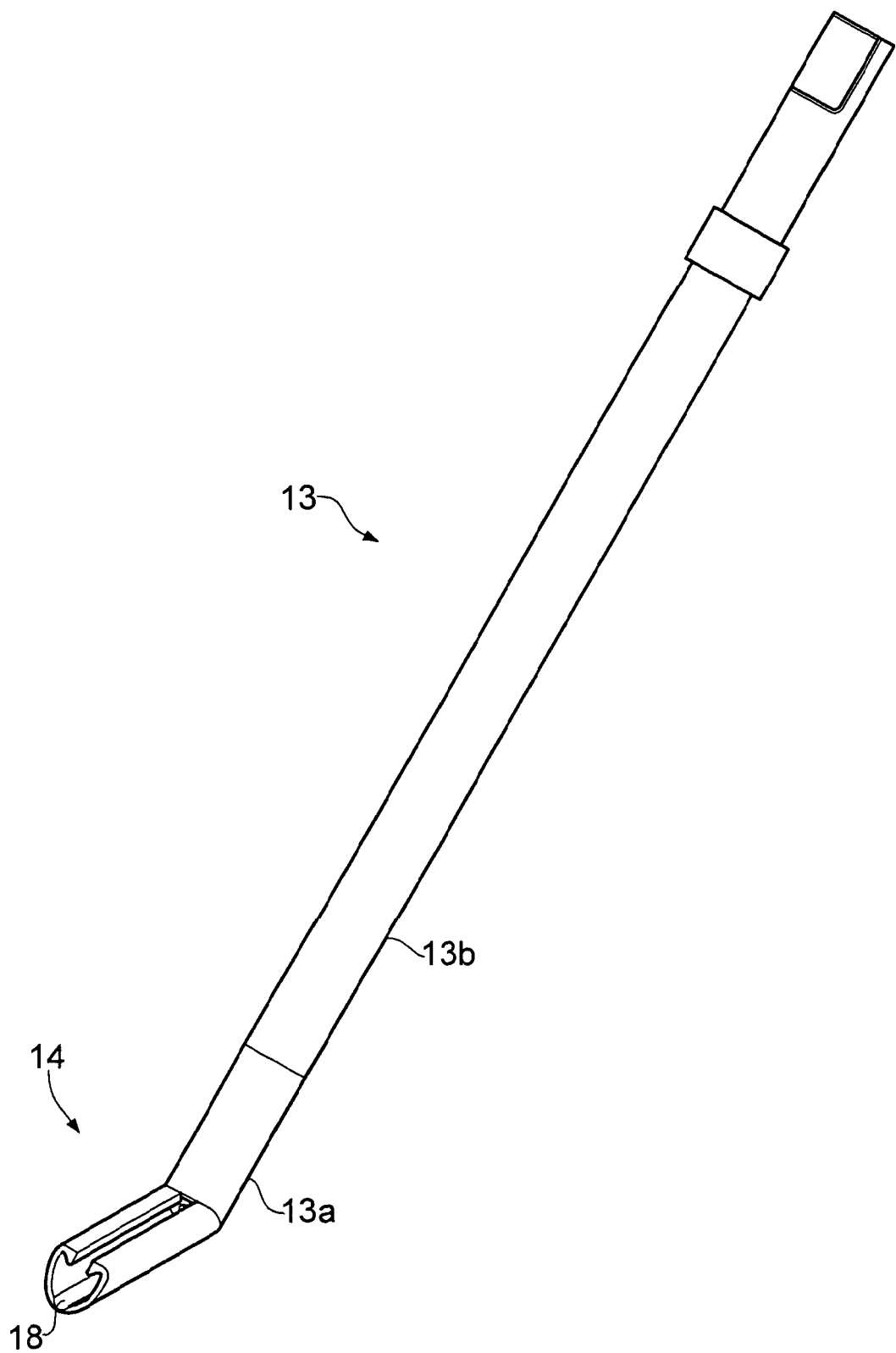
FIG. 2 shows the tip portion of the first embodiment of the device.

FIG. 2 is a diagram of the tip portion 13 when detached from the handle 11. The tip portion 13 may itself be made from two separately moulded or machined components 13a and 13b. These components 13a and 13b may be attached together by a press-fit or suchlike. The tip portion 13 may be elongated and narrow so that the distal part 13a of the tip portion (comprising the head portion 14) can be easily inserted into the eye. The tip portion 13 may also be hollow so that an urging member, for example a wire, suture, string or conveyer belt, can be inserted into the proximal end of the tip portion 13 and move within the inside of the tip portion 13 along its longitudinal direction, so as to appear at the distal end and engage with a carried implant there. The tip portion 13 is preferably mounted in the handle 11 so as to be rotatable around the longitudinal axis when in an unlocked configuration. This allows the user of the device 10 to adjust the location of a head portion 14 of the tip portion 13 relative to the handle 11. The tip portion 13 can be rotated about the longitudinal axis in accordance with the required location for implanting the implant in the eye. Preferably, the tip portion can be rotated 90°, more preferably 180°, even more preferably 270° C. and even more preferably 360° or greater. The tip portion 13 may be locked into the desired configuration when being used to deliver the implant. The tip portion 13 can be locked and unlocked by respectively tightening and loosening of screws in the handle 11 which can contact the end of the tip portion 13 inserted in the handle 11.

Figure 3:
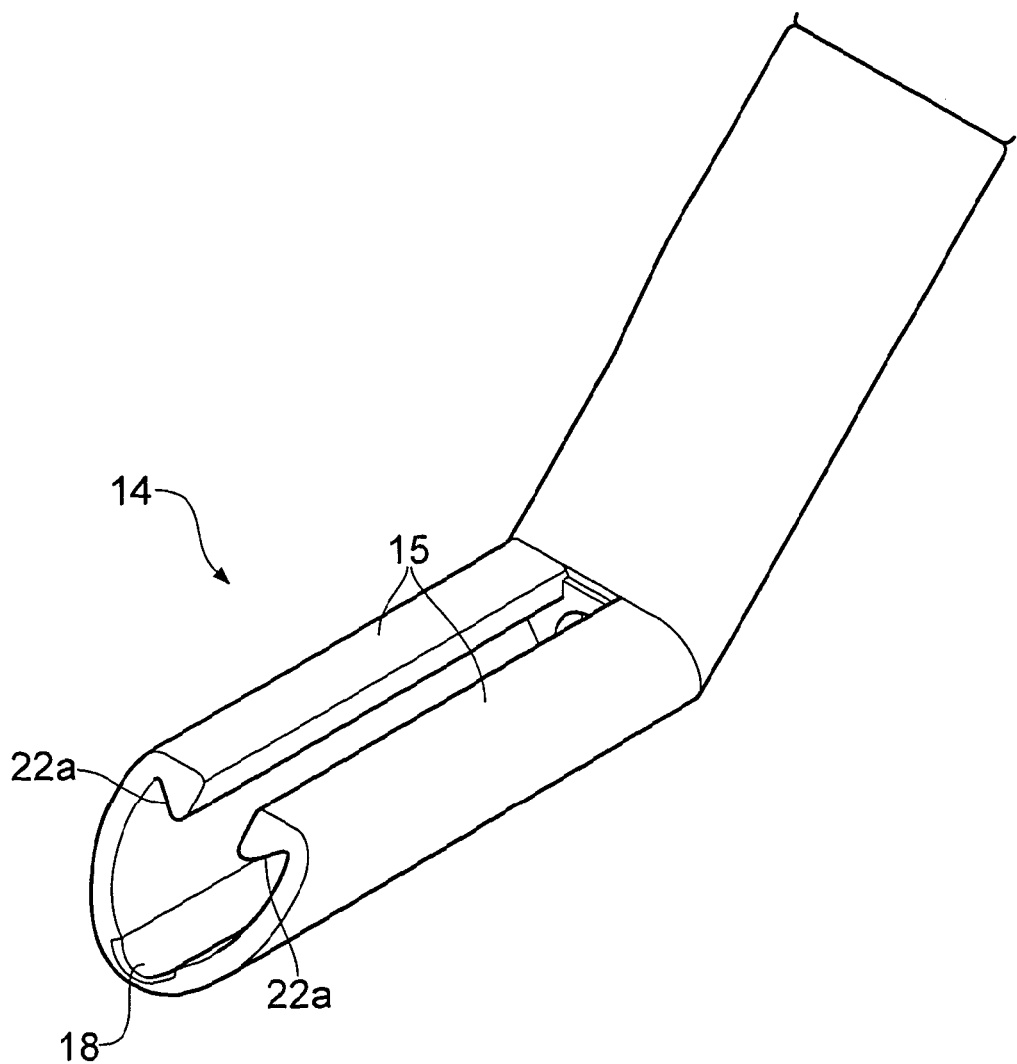
FIG. 3 is a close-up of the head portion of the first embodiment of the device.

FIG. 3 shows a close-up of the head portion 14 of FIGS. 1 and 2. In this first embodiment, the top of the head portion 14 is formed to be substantially flat. The top of the head provides two ledges that face inwardly and help to retain the implant in place inside the head portion 14. The head portion 14 comprises side walls 15 that are curved and extend generally upwardly, before folding over to face one another at the top of the head portion 14.

Figure 4:
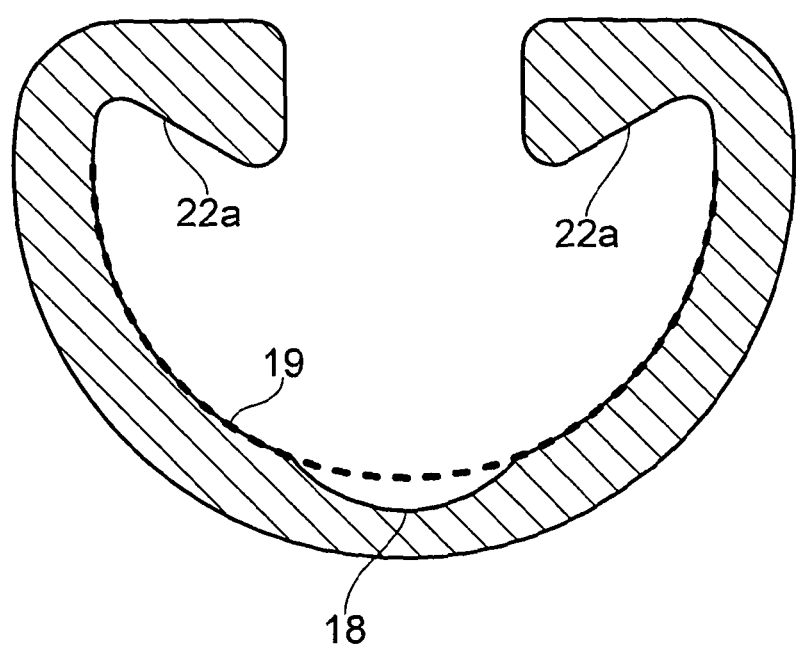
FIG. 4 is a cross-section through the head portion of the first embodiment.

FIG. 4 shows a cross-section through the head portion 14 of the first embodiment, with an implant 19 shown located in position in the head portion. Numeral 18 depicts a guiding means, which in this embodiment comprises an elongated groove that runs longitudinally along the bottom surface of the head portion. Accordingly, the guiding means 18 extends in a direction parallel to the direction of deployment of the implant 19.

Figure 5:
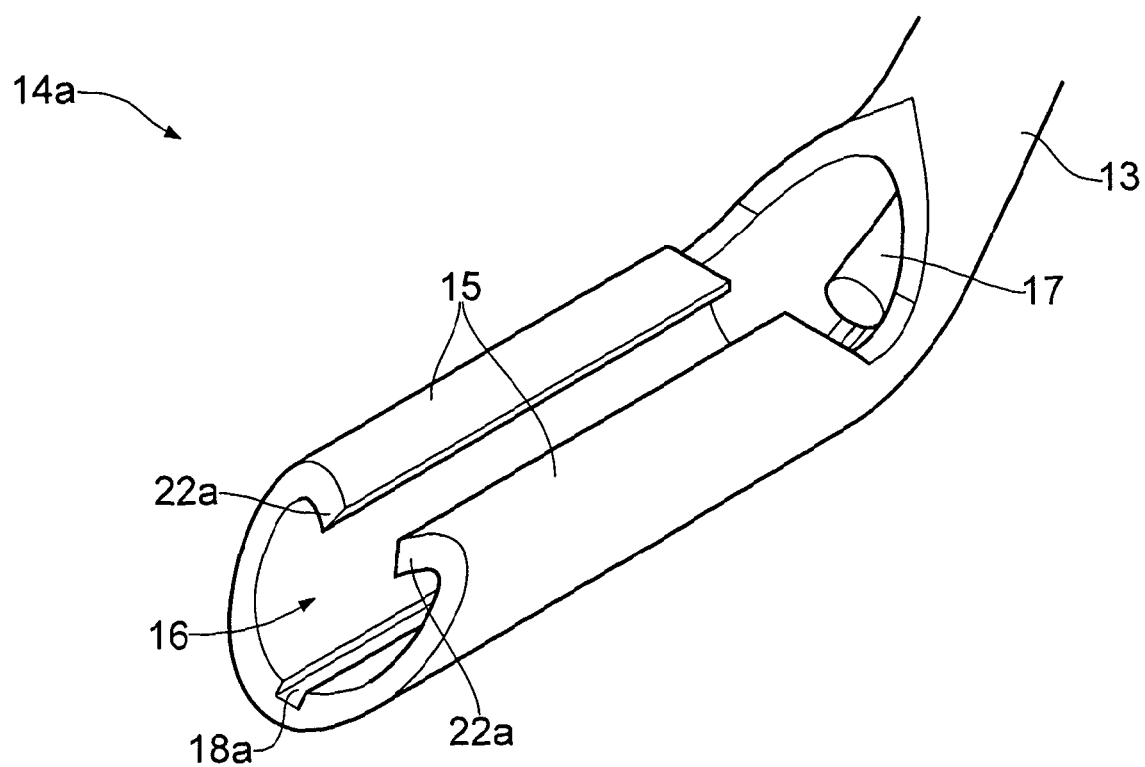
FIG. 5 is a close-up of a head portion of a second embodiment of the device.

FIG. 5 is similar to FIG. 3 but shows an alternative form for the head portion of the tip portion 13 according to a second embodiment of the invention. The head portion 14a of the second embodiment also comprises curved walls 15. As with the first embodiment, the end of the head portion may have an opening 16 which can be formed by the sides of the curved walls 15. The tip portion 13 and the end opposite to the opening 16 of the head portion 14a may each comprise an opening for an urging member, for example, a wire or suture 17, to enter the head portion 14*a*. By providing an urging member that is routed through the centre of the tip portion, the tip portion is allowed to rotate around the urging member with respect to the handle. The head portion 14*a* may also comprise a guiding means 18*a* for guiding the urging member 17 centrally along the head portion 14*a*. The guiding means 18*a* preferably extends along a part of the tip that is underneath the implant when it is carried, thereby allowing the urging member 17 to be effectively guided for the whole time that the urging member 17 is in contact with the implant during deployment. The embodiments of FIG. 3 and FIG. 5 each have a groove 18, 18*a* as the guiding means. The guiding means may also be formed by any suitable means, including walls, guide posts or such like.

The walls 15 of the first and second embodiments extend in a generally longitudinal direction, parallel to the direction of deployment of the implant. They curve over themselves towards their top portion and come close to one another at the top, although they do not touch. The walls curve in a plane that is generally transverse to the deployment direction. Preferably, the walls do not curve parallel to the deployment direction. As such, the walls 15 generally provide a tunnel-shaped space for carrying the implant, whereby the implant may be inserted and deployed from the opening 16 formed by the distal parts of the walls 15. The shape of the walls is such as to cause a carried implant to the curve in a direction generally transverse to the deployment direction. In addition, the walls are so shaped as to preferably not cause any curvature of the implant in a direction parallel to the deployment direction.

Accordingly, the head portion 14, 14*a* of the tip portion 13 is constructed and arranged to accept and carry a planar flexible implant, to cause that flexible implant to the curve, preferably in a direction transverse to the deployment direction, and to allow an urging member to come into contact with the flexible implant so as to move the implant from the carried position to a deployed position.

In the first embodiment, the walls may preferably comprise one or more retaining lips 22*a* (see FIG. 3). These retaining lips 22*a* also help to restrict movement of the implant in the same way as the curved walls 15 of FIG. 5. If the implant moves, the edge of the implant contacts a retaining lip 22*a* and is prevented from further transverse movement. The lips 22*a* may be formed at an angle such that they do not contact the surface of the implant, but only the edge of the implant. The lips 22*a* may be provided by the edges of the walls 15, as in the second embodiment.

The head portion 14 of FIGS. 1, 2 and 3 has approximately the same internal configuration as the head portion 14*a* of FIG. 5. However, the external configuration is slightly different, as can be seen by comparing the drawings. In particular, the configuration of the first embodiment is more shrouded and less open to the outside, and is preferred for this reason. The first embodiment also has a wider guiding means 18 that has a circular radius. The guiding means 18*a* of the second embodiment is square-edged. This is not a limiting feature of the invention and any shape of guiding means 18, 18*a* may be used in any embodiment.

Figure 6:
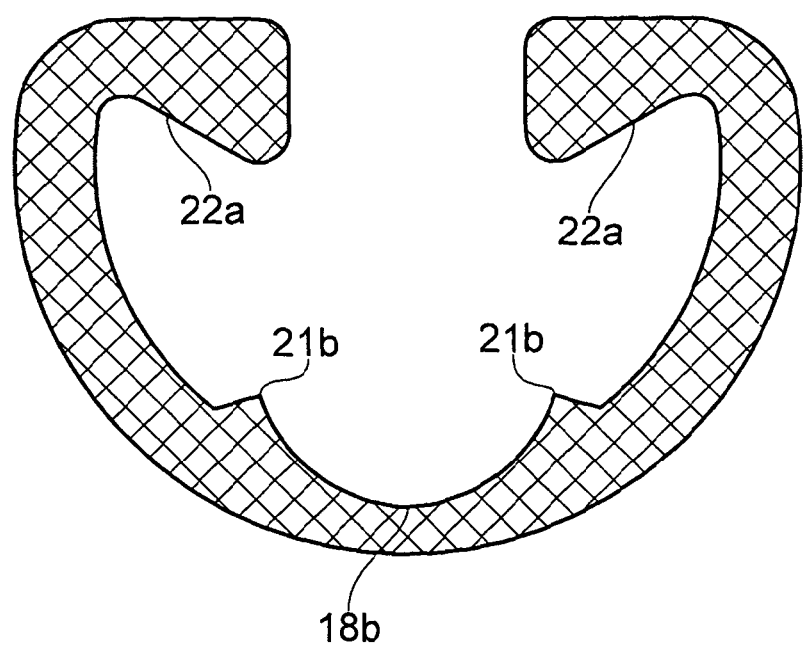
FIG. 6 is a cross-section through a head portion of a third embodiment of the device.

FIG. 6 shows a cross section of a third embodiment of a head portion. The design is similar to the first embodiment (see FIG. 4 in particular), although a slightly modified guiding means is shown. In this embodiment, the guiding means comprises support lips 21*b*. In particular, the edges of the guiding means 18*b* are preferably raised to form the lateral support lips 21*b*. The lips 21*b* act to surround the urging member in use and to further restrict the movement of the urging member transversely of the longitudinal direction of the groove 18*b*. This provides greater accuracy in guiding the urging member. In turn, the deployment of the implant is more reliable.

The urging member of the invention is preferably elongated. The urging member is usefully connected to the actuating member 12 so that actuation of the actuating member causes the urging member to urge the implant, for example by advancing down the middle of the tip portion 13. The urging member may be a wire 17. The wire may be a suture, or the wire may be made from nylon or from a nickel titanium alloy. The urging member may also be a coiled wire. Alternatively the urging member may be a hydraulic piston.

As will be evident from the Figures, the urging member preferably bends as it advances down the inside of the device. A urging member formed as a coiled wire facilitates this bending and it has been found that a coiled wire goes around the corner more easily than a simple wire. Further, when a coiled wire is again retracted, it returns to its original shape, whereas a simple wire may be plastically deformed when going around the corner.

The urging member preferably has an overall diameter of 1 mm or less, more preferably in the range 0.5 mm-0.9 mm. If a coiled wire is used, the wire itself can preferably have a diameter in the range 0.1 mm-0.2 mm, with the overall diameter of the coil being in the range 0.5 mm-1.0 mm.

The end of the urging member that contacts the implant is preferably ground or otherwise flattened. This increases the chance of successful implant deployment.

All edges in the head portion 14 may preferably be blunted so that the edges do not cause damage to the eye upon insertion or retraction therefrom. This can be achieved by way of grit-blasting or similar.

The guiding means of all embodiments of the invention may be a groove that conforms to the shape of part of the urging member. As shown in FIGS. 4 and 6 the groove 18, 18*b* may be curved. The curvature of the groove 18, 18*b* may be the same as the curvature of the urging member (such as a suture, wire or a coiled wire). This ensures that the urging member fits into the groove 18, 18*b* so that the urging member can be accurately guided. As will be apparent from the Figures, the guiding means 18, 18*a*, 18*b* allows the urging member to move substantially along the longitudinal direction, so as to push any implant located in the head portion 14, 14*a* outwards from the device, but also helps to restrain movement in the transverse directions (i.e. directions perpendicular to the direction of implant deployment).

The urging member 17 can be guided along the head portion 14, 14*a* by the guiding means, such as a groove 18, 18*a*, 18*b*. The guiding means 18, 18*a*, 18*b* helps restrain movement of the urging member 17 to a direction that is along the longitudinal axis of the head portion. The guiding means 18 may also help the urging member 17 to remain rigid. Furthermore, as the guiding means may be slightly depressed into the head portion 14, the implant 19 may rest on top of the guiding means 18, 18*a*, 18*b* (for example see FIG. 4). The guiding means therefore does not interfere with the smooth movement of the implant 19 into and out of the device 10.

The urging member 17, which in use runs along the guiding means 18, 18*a*, 18*b*, can be arranged to contact the edge of the implant 19 someway above the bottom edge of the urging member 17. It is particularly preferred that the implant edge is positioned close to the midline of the end of the urging member. This is due to the guiding means providing a space for movement of the urging means below the implant, as shown in FIG. 4. Thus the guiding means 18,

18a, 18b may guide the urging member 17 so that the end of the urging member is directed in a direction that is perpendicular to the edge of the implant (and/or perpendicular to the plane of the implant). This helps ensure that the end of the urging member 17 contacts the edge of the implant 19 and helps avoid the urging member altogether missing the edge of the implant 19 or being forced above the edge so that the urging member undesirably runs along the top surface of the implant 19. Also, by providing a guiding means so that the edge of the implant 19 contacts the end of the urging member towards the central, wider portion of the cross section of the urging member, the contact area between the edge of the implant and the end of the urging member can be increased. This helps to prevent the urging member from slipping above the edge of the implant. Thus deployment of the implant is more reliable.

Figure 7:
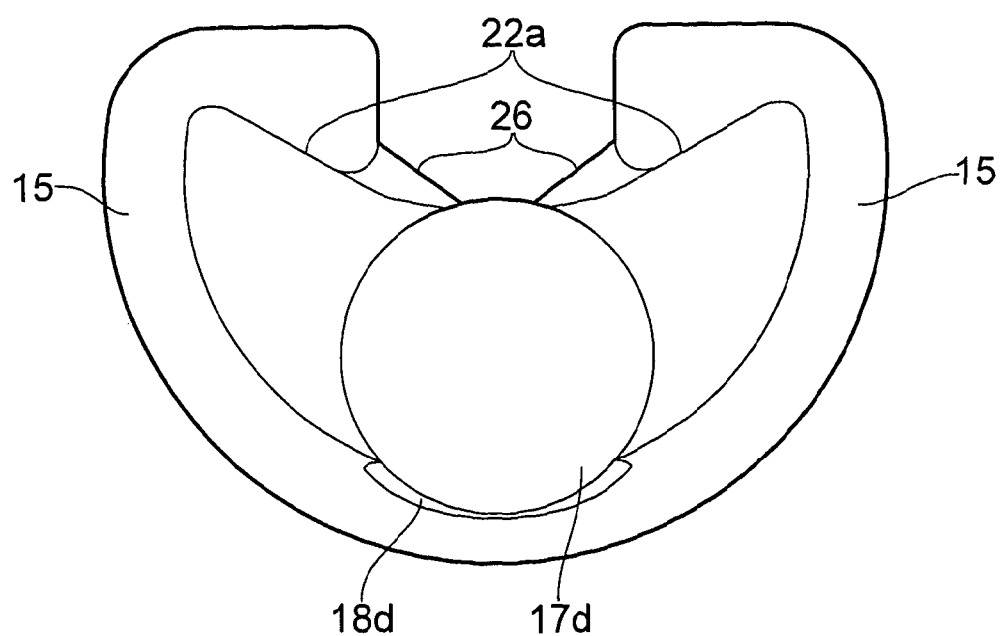
FIG. 7 is a cross-section through the head portion of a fourth embodiment of the device.

In a fourth embodiment, longitudinal guiding ribs 26 may be provided, as shown in FIG. 7. These guiding ribs 26 can contact a surface of the urging member 17d that is generally opposite to that at which the guiding means 18d contacts the urging member 17d. This helps to additionally guide and secure the urging member 17d inside the device as it moves. The support ribs 26 may be provided along the walls 15, be an extension of the walls 15, may be formed continuously along the walls 15 or at certain points along the walls 15 of the head portion 14. The guiding ribs 26 may be formed at the end of the head 14b at which the head is attached to the longitudinal part of the tip (i.e. opposite to the opening 16). This would help to initially guide the urging member 17d so that it properly sits on the guiding means 18d.

The urging member 17 need not be intimately surrounded by the head portion 14, 14a, 14b along its full length. The cross section of the urging member 17 may clearly be different to the cross section of the implant. As depicted herein, the urging member 17 has a substantially circular cross-section while the implant 19 has a very elongated rectangular cross-section. Other shapes are however possible.

FIGS. 8 and 9 are diagrams of the device, similar to FIG. 1, with the handle removed or partially removed to show how the tip portion can be connected to the actuator 12 or handle 11. In FIG. 8, one end of the urging member 17 is fed into the hollow tip member 13 and the other end of the urging member 17 is secured to the back of the wheel 12, for example by means of a set screw 52 (see FIG. 9). The wheel 12 may have a circumferential groove 54 which further secures the urging member 17 so that the urging member 17 does not axially or transversely move with respect to the wheel 12. As the wheel 12 rotates, the urging member 17 either unwinds or winds around the wheel 12. In the example of FIGS. 8 and 9, clockwise rotation of the wheel 12 would unwind the urging member 17, thus extending the urging member 17 into the tip portion. Thus, rotational movement of the wheel can cause linear movement of the implant as the urging member extends down the tip and head portions. Anticlockwise rotation of the wheel 12 would cause the urging member to wind around the wheel and therefore partially retract from the tip portion 13. The tip portion 13 and the wheel 12 are, in use, a fixed distance away from each other so the urging member 17 moves relative to the tip portion 13. The urging member could be wound around the wheel in an opposite direction. This would cause the urging member to extend into the tip portion when rotated anticlockwise. It is particularly advantageous that, whatever the configuration of the actuator, the direction of movement of the actuator in order to extend the urging member is opposite to the direction in which the device is moved in order to introduce it into the eye. For example, where the actuator is a wheel, the wheel is preferably rotated away from the tip region to advance the urging member. This helps to prevent accidental advancement of the urging member.

The wheel 12 may further comprise a means 48, 50 to limit rotation so that the urging member 17 does not extend too far beyond or within the head portion 14a, thus avoiding damage to the eye which may be caused by the urging member. The movement of the wheel may be limited by a pin 48 located on the wheel 12 that runs inside a guide slot 50 located inside the handle, and which abuts the pin 48 once a certain amount of rotation has been achieved.

The rotational movement of the wheel 12 causes the urging member 17 to move, which in turn causes the implant 19 to move linearly. Rotating a wheel may help provide smoother urging of the implant 19. This may help prevent the implant 19 from crumpling due to rapid application of force by the urging member due to unsmooth actuation. This helps provide greater control when deploying the implant.

As mentioned above, it is preferable that the top surface of the implant 19 does not come into contact with any part of the device or any other implant as this may remove or damage the medicament on the top surface. Thus by providing an urging member 17 that contacts the edge of the implant 19 and not the top surface of the implant, damage to the medicament can be avoided. Furthermore, as the implant is secured to the device by flexing the implant into a curved configuration so that an elastic force is provided between the bottom surface of the implant and the head portion 14, there is no requirement for the top surface of the implant to be touched when securing the implant to the device. Furthermore, as the walls 15 can be curved around the edges of the implant 19, but without contacting the top surface of the implant, the implant is further secured to the head portion 14, 14a, 14b while avoiding contact of the device to the top surface of the implant. The ends of the walls 15 may point towards the median plane of the head portion 14, 14a, 14b. The median plane is a plane that divides the head portion into symmetrical halves.

The device may be formed into a hockey-stick shape. As such, the longitudinal axis of the handle and/or tip may be different to the longitudinal axis of the head portion. Preferably, the angle between the longitudinal axis of the head portion and the longitudinal axis of the tip and/or handle is between 10° and 80°, preferably between 20° and 70°, preferably between 30° and 50°, more preferably between 40° and 50° more preferably being about 45°. This angle is shown in the figures as angle A. This angle allows easier manipulation of the head portion when within the eye, particularly when deploying an implant in the curved walls of the eye. The heel or corner between the two portions is preferably curved rather than being a sharp corner. The corner is preferably curved both internally and externally to allow easy movement of the urging member around the corner and also easy, less traumatic entry of the device into the eye.

The tip portion 13 (with the head portion) may be removably attachable to the handle 11. This allows the handle to be reused and the tip portion to be discarded for the purposes of hygiene.

Figure 10A:
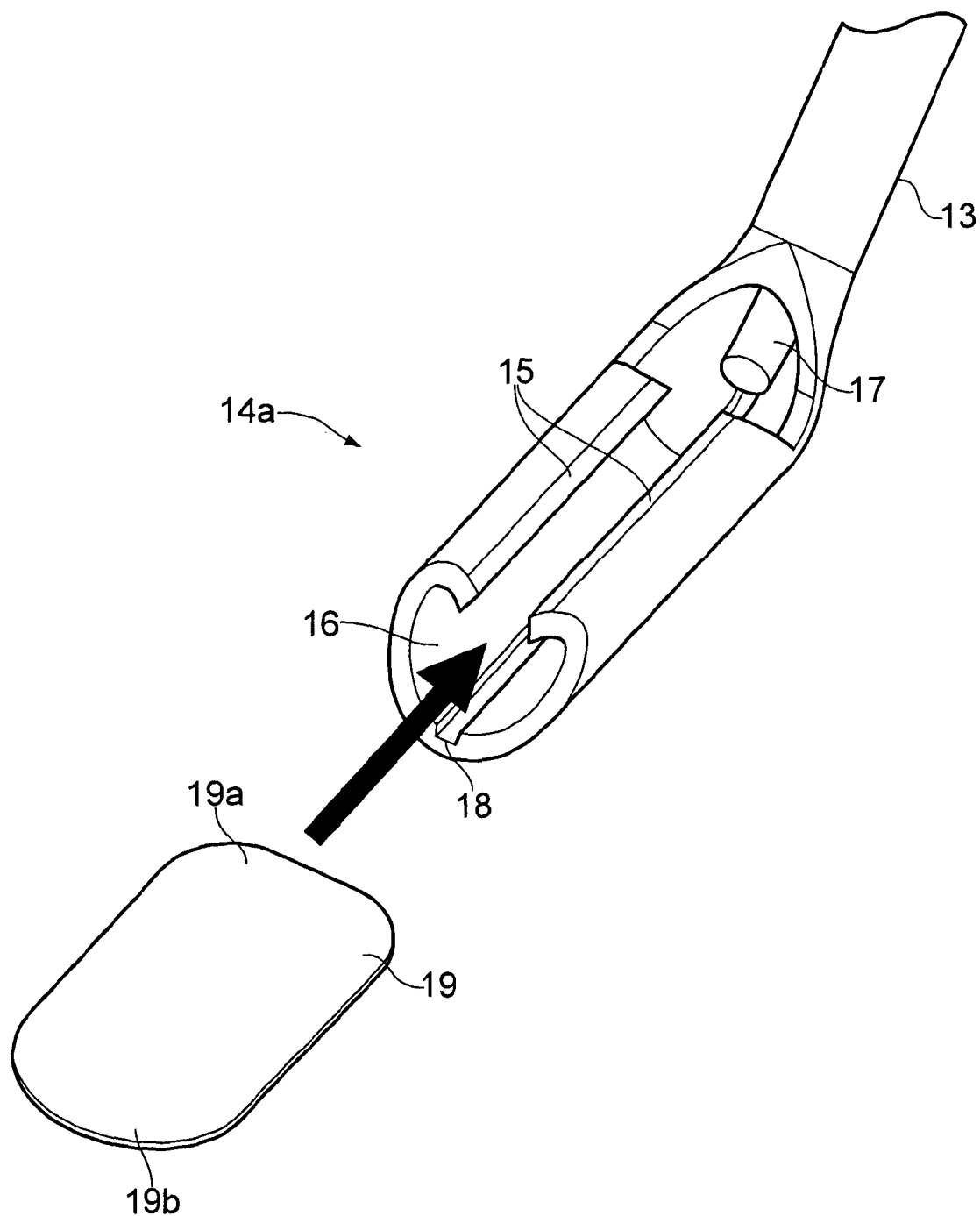
FIGS. 10A to 10C depict the insertion of an implant into the head portion of the second embodiment.
Figure 10B:
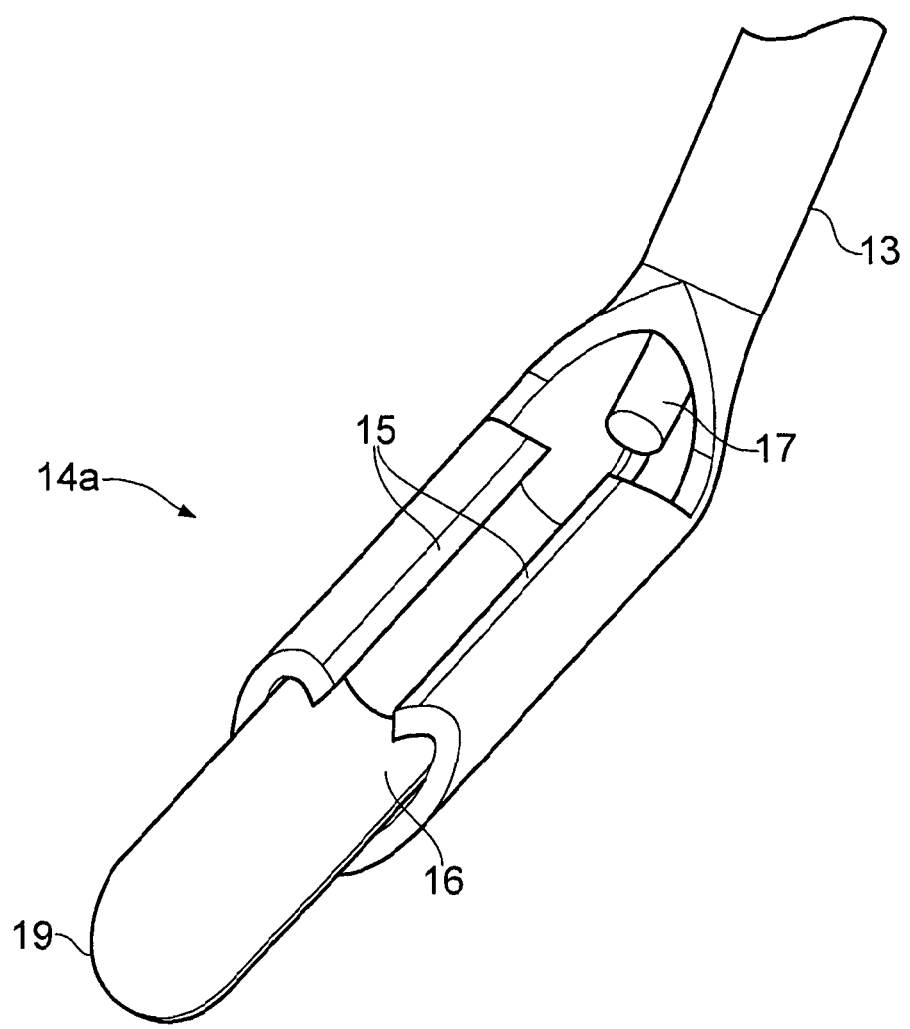
Figure 10C:
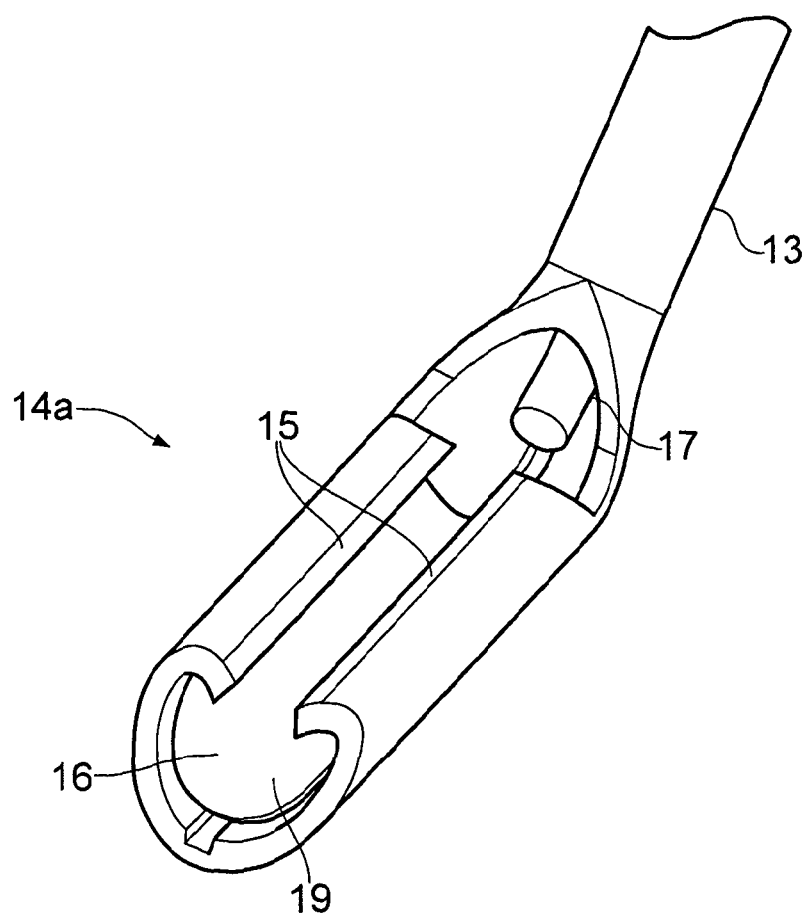

FIGS. 10A to 10C depict the process of loading an implant 19, for example a patch, into the head portion 14 of the FIG. 3 embodiment of the device 10. The process is substantially the same as for the other embodiments and can be applied thereto without further explanation being necessary.

FIG. 10A shows an embodiment of an implant 19 which is substantially flat and substantially planar. The implant 19 may preferably be flexible and this may be achieved by forming the implant 19 from a flexible plastic, such as PET (available as Dacron™). In general, any material may be used if it provides for an implant that is thin, flexible and able to be deformed into the shape of the inside of the head of the device.

The implant is generally rectangular and may have dimensions of about 3 mm×6 mm. The short sides of the implant here have different shapes, with one end 19a being squarer than the other end 19b. The more square shape of end 19a allows easier insertion and curling of the implant into the device 10. The more curved end 19b allows easier deployment of the implant into the eye or other target location. The implant 19 may have stem cells or any other active agent or medicament placed or formed on one or more surfaces of the implant 19. The implant 19 may have a medicament formed within it, or may be formed by the medicament itself. The implant may be a drug eluting implant or a radioactive source.

In some cases where the medicament is formed on a surface (e.g. the top surface), it may be preferable that the top surface of the implant does not come into contact with any part of the device or any other implant as this may contaminate, damage or remove the medicament (such as stem cells) from the implant 19. In other cases (depending on the medicament), a surface with a medicament may contact the device.

As shown by the arrow in FIG. 10A the implant 19 may be inserted into the head portion 14 in a direction that is substantially parallel to the longitudinal axis of the head portion 14. The opening 16 of the head portion 14, 14a, 14b may be angled away from a plane that is perpendicular to the direction of insertion of the implant 19, as shown in FIG. 10A. The plane perpendicular to the plane of insertion is shown in the figures as the plane X-X. Preferably, the plane of the opening forms an angle of around 10 to 80°, preferably 20 to 70 more preferably 30° to 60° even more preferably 45 to 55° from the plane of the direction that the implant 19 is inserted into the head portion 14, 14a, 14b. The inventors have found that an angle of about 50° works particularly well. This is shown in the figures as angle B.

As the implant is inserted into the head portion 14, 14a, 14b, the leading edge of the implant 19a contacts the walls of the opening 16 (preferably, the walls of the opening 16 being the sides of the curved walls 15). Due to the angle between the plane of the implant 19 and the plane of the opening 16, the implant automatically flexes into a curved configuration as it is being inserted.

FIG. 10B shows the implant being inserted through the opening 16 and being part-way into the head portion 14, 14a, 14b. As can be seen, once the implant has been inserted by a small amount, it assumes a curved configuration that generally corresponds to the internal curvature of the interior walls of the head portion 14, 14a, 14b. The curvature is in a plane perpendicular to the direction of deployment of the implant. FIG. 10C shows the implant 19 fully inserted into the head portion 14a and in the carried configuration. When the implant is fully inserted into the head, it is in a curved position and the curvature of the implant 19 preferably conforms to the inside curvature of the head portion 14, 14a, 14b. The implant is flexed when it is curved. The implant 19 may be secured in the head portion 14, 14a, 14b by contact of only the bottom surface of the implant 19 with the internal surfaces head portion 14, 14a, 14b. The implant 19 may thus be secured in place by an elastic force applied by the implant 19 (due to the elasticity of the implant 19) to the head portion 14, 14a, 14b. The walls of the head portion 14, 14a, 14b may be curved, as shown. The curved walls 15 can help secure the implant 19 in the head portion 14, 14a, 14b. The curved walls 15 are preferably curved over the transverse edges of the implant 19 so as to restrict movement of the implant in transverse directions. The walls are preferably curved over the edges of the implant 19 so that if the implant moves, only the edges of the implant 19 come into contact with the curved walls 15 and not the top surface of the implant 19. As seen in FIG. 10C, the curvature of the walls 15 increases near the edges of the implant, so as to firmly hold the implant in place. Instead of curved walls per se, lips 22a may be provided, as shown in FIG. 3.

The implant 19 may be inserted into the head portion 14, 14a, 14b by pushing the implant 19 into the opening 16. Alternatively, the implant may be pulled, by, for example, a pair of micro forceps, into the head portion 14, 14a, 14b. The micro forceps may run along the gap between walls 15 when pulling the implant 19 into the head portion 14, 14a, 14b.

Figure 11A:
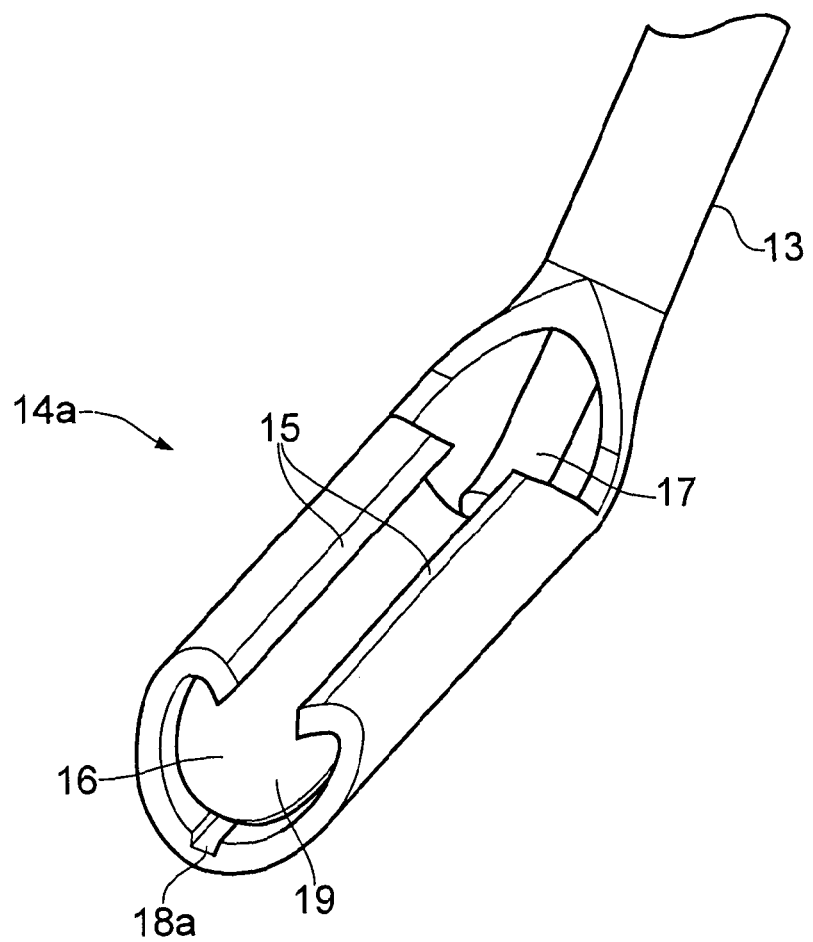
FIGS. 11A to 11C depict the deployment of the implant from the head portion of the second embodiment.
Figure 11B:
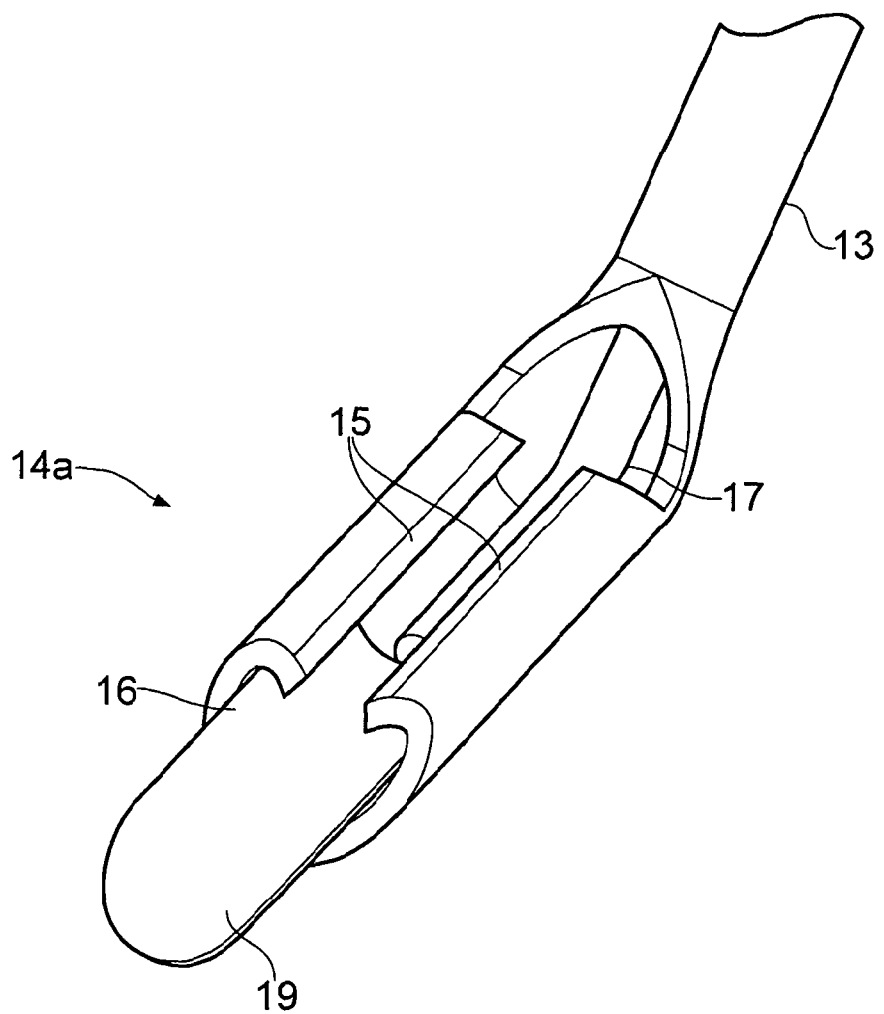
Figure 11C:
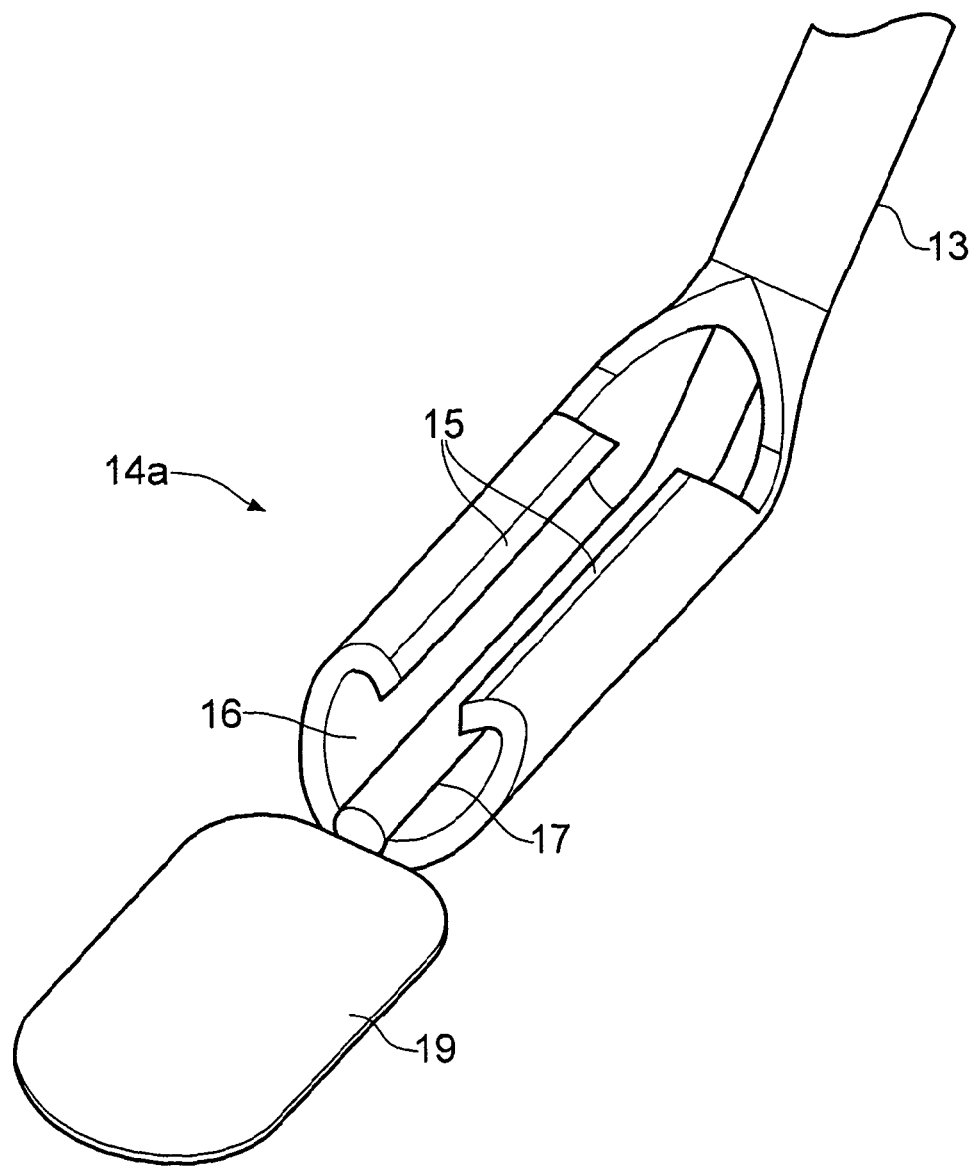

FIGS. 11A to 11C depict the process of deploying the implant 19 from the head portion 14, 14a, 14b of device 10. The implant is designed to linearly move down the head portion when being deployed. The urging member preferably causes the necessary linear movement.

Initially, actuator 12 is actuated so as to present the urging member 17 into contact with an edge of the implant 19, as shown in FIG. 11A. Movement of the urging member 17 is controlled by the actuator, such as the wheel 12. The urging member generally follows the path of the guiding means 18a as it moves, thereby assuring proper movement in the correct deployment direction. As shown in FIG. 11B, as the urging member moves along the head portion 14, 14a, 14b, it pushes the implant 19 out of the opening 16, thereby deploying it. The urging member 17 is preferably continuously guided by the guiding means 18, 18a, 18b for the duration of the time that it remains in contact with the implant 19. This is preferably achieved by routing the urging member underneath the implant. As the implant 19 is in a curved configuration, the implant is more rigid along its longitudinal axis and therefore, when the pushing force is applied to the edge of the implant 19, the implant 19 maintains its structural integrity and does not crumple along its longitudinal axis. As the implant 19 exits the head portion 14, 14a, 14b of the device 10, the implant may begin to flatten. As shown in FIG. 11C, when the implant 19 has fully exited the head portion (i.e. when in the deployed position), the implant 19 can flex back (under its own elastic force) into a flat configuration. The shape of the implant may conform to the shape of the surface to which it has been deployed. For example, if the implant is deployed in the back of the eye the implant may end up being curved to conform to the curvature of the back of the eye.

The angled opening 16 may additionally help deployment of the implant 19. When a part of the implant 19 has left the angled opening 16 the part can begin to flatten, under the implant's own elastic restoring force. This itself exerts a force onto the angled opening and thus can help assist the implant further out of the head portion. Thus, the urging member 17 may not be required to completely push the implant all the way out of the head portion 14, 14a, 14b, and may have it's travel limited to a certain proportion of the way along the head portion.

Figure 14A:
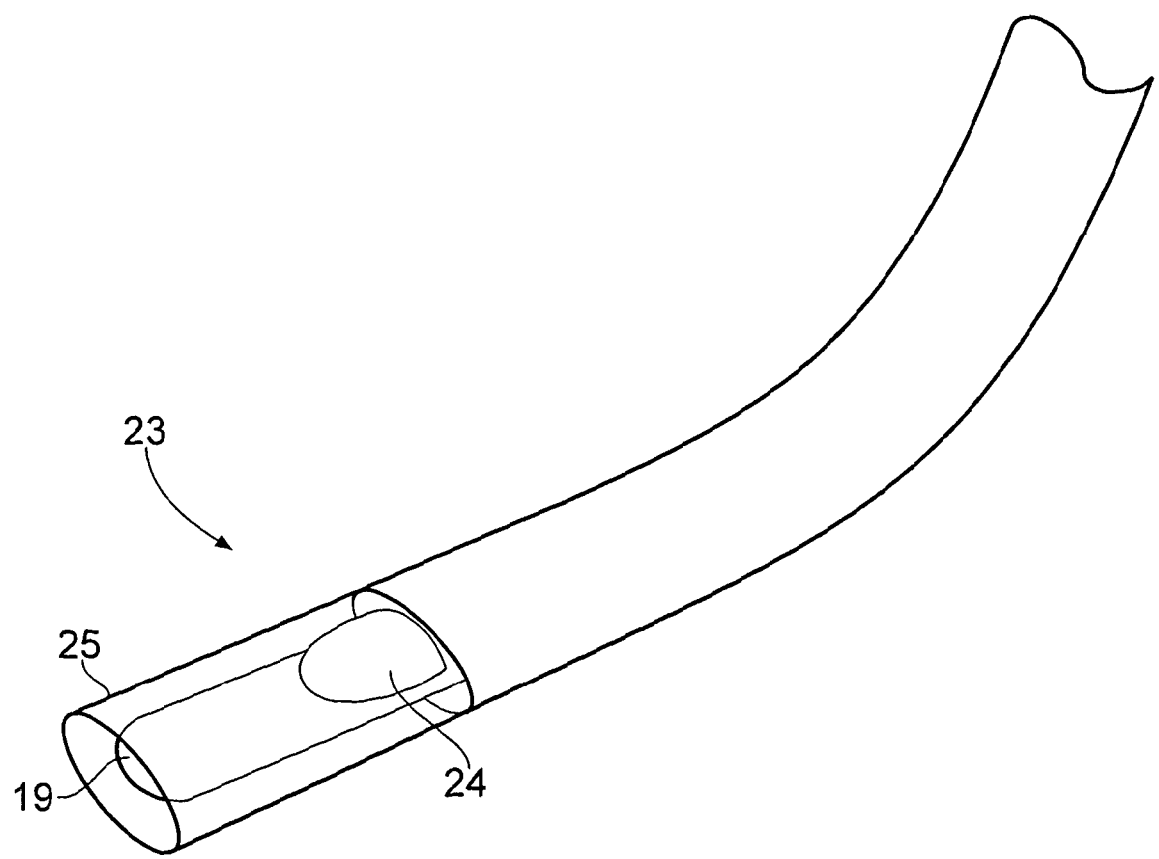
FIGS. 14A and 14B show a fifth embodiment of the device.
Figure 14B:
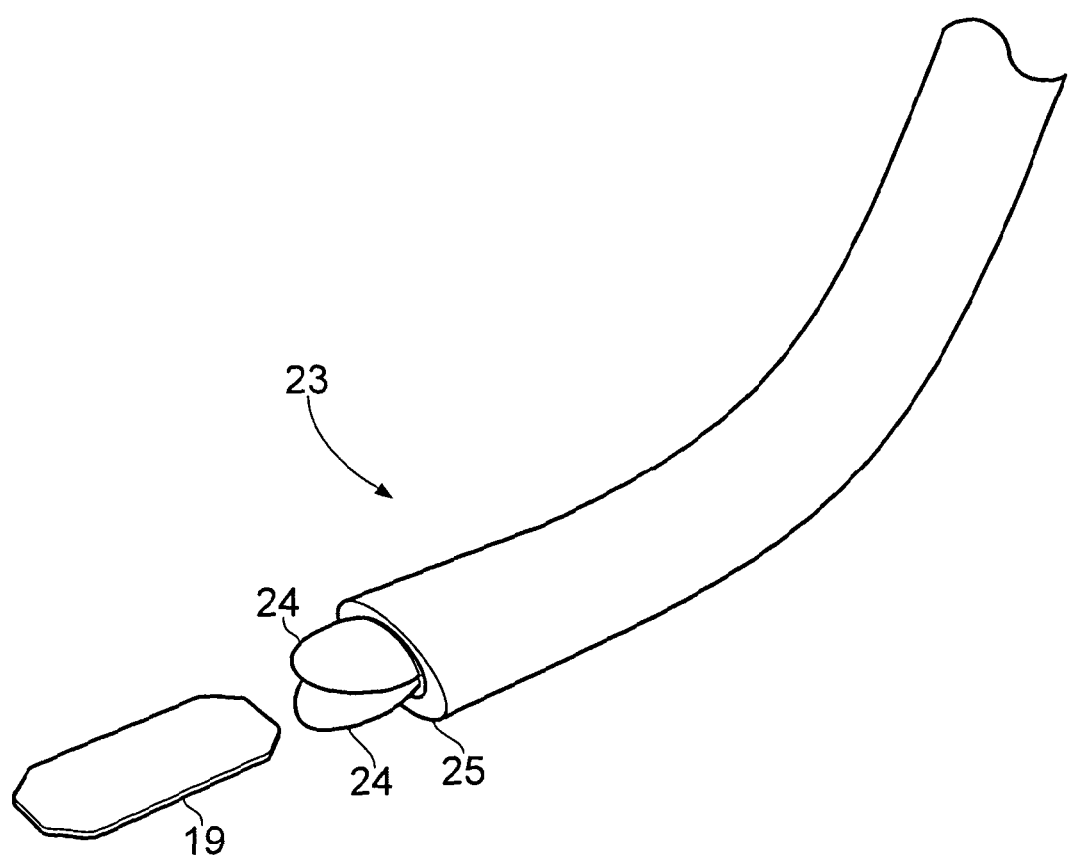

FIGS. 14A and 14B show a fifth embodiment having an alternative design of head portion 23 in which a pair of holder jaws 24 grip the implant 19. An outer sheath 25 can be used to force the holder jaws 24 together so that they grip the implant. Alternatively, the holders 24 can be forced to grip the implant by any other mechanism. In one embodiment, as the outer sheath 25 is pulled back (in the direction from the distal end to the proximal end), the holders separate (as shown in FIG. 14B), and release the implant. The outer tube can be activated by using the wheel mechanism, for example. The rotational movement of the wheel can cause the end of the sheath 25 to move linearly relative to the implant. Alternatively, in another embodiment the holder jaws 24 and the implant 19 can be linearly moved down the inside of the outer sheath 25 when activated (by, for example, a wheel).

FIGS. 15A and 15B show a sixth embodiment of the device which utilises a conveyor mechanism as the actuator and urging member. A thumb actuated conveyor belt 60 is provided as the actuator. The actuator 60 is connected to a modified head portion 14b that contains a conveyor belt. As shown in FIG. 15B, the implant 19 is carried on the head conveyor belt 62 within the confines of the device. In FIG. 15B, the implant 19 is shown in a partially deployed position. Movement of the actuator 60 causes the conveyor belt 62 to move (anti-clockwise as shown in FIG. 15B) and this in turn causes the implant 19 to be deployed from the device.

In order to insert the implant into the device, it is merely necessary to present the edge of the implant 19 to the opening in the head portion 14b and move the actuator 60 in the opposite direction, so as to feed the implant 19 from a deployed position to a carried position inside the device.

FIGS. 16A and 16B show a seventh embodiment of the invention. In this embodiment, the actuator is a string 70 that runs down the length of the tip portion 13 to modified head portion 14c. The head portion 14c is shown in more detail in FIG. 16B, where the implant 19 is shown in a partially deployed position.

As can be seen from FIG. 16B, the string 70 runs to the distal end of the head portion 14c, where it is fed around a small pulley (not shown) and is terminated by a hook 72. The hook 72 engages with the implant 19 and, pulling on the string 70 causes the implant to move from a carried position (located inside the vice) to a deployed position (located outside of the device).

The hook 72 automatically disengages from the implant 19 when it reaches the pulley.

It will be appreciated that various different embodiments of the invention have been described. Various features of one embodiment may be used in combination with features of the other embodiments. For example, all embodiments of the invention may provide that the implant is curved, preferably in the transverse direction, during the carried position. Further, all embodiments of the invention may use an urging member and a guiding means to deploy the implant. Various other possible modifications will be apparent to the skilled person.

The invention also includes a method of loading and deploying the implant, as described above.

Figure 12:
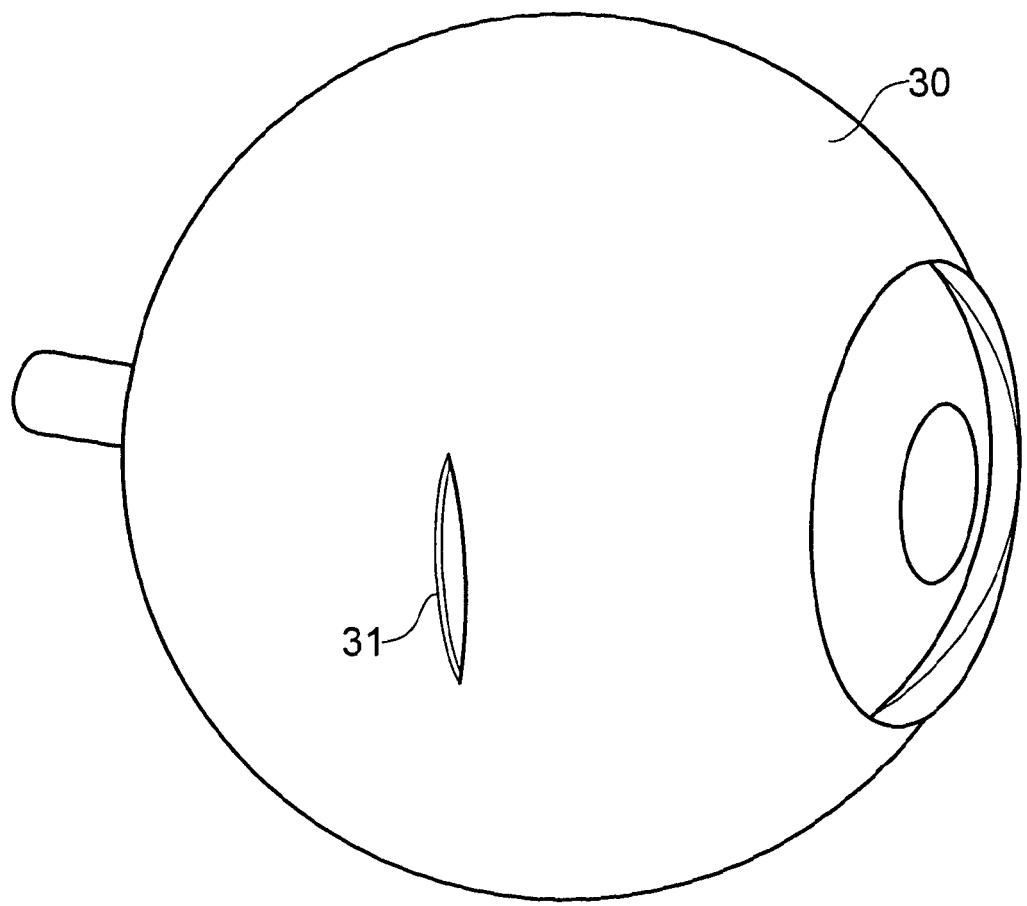
FIG. 12 is a diagram of an eye with an incision made for insertion of the device.

FIG. 12 shows a diagram of an eye 30 with a slit 31 formed therein, in a position typical for inserting the implant of the invention using the device of the invention. The angle between the head portion and the handle of the device allows the slit 31 formed in the eye to be narrow. The size of the slit may also correspond to the size of the head portion 14. As the implant 19 is forced into a curved configuration when carried inside the head portion 14, an implant of a larger width can be introduced into the eye while providing a small sized slit 31.

Figure 13:
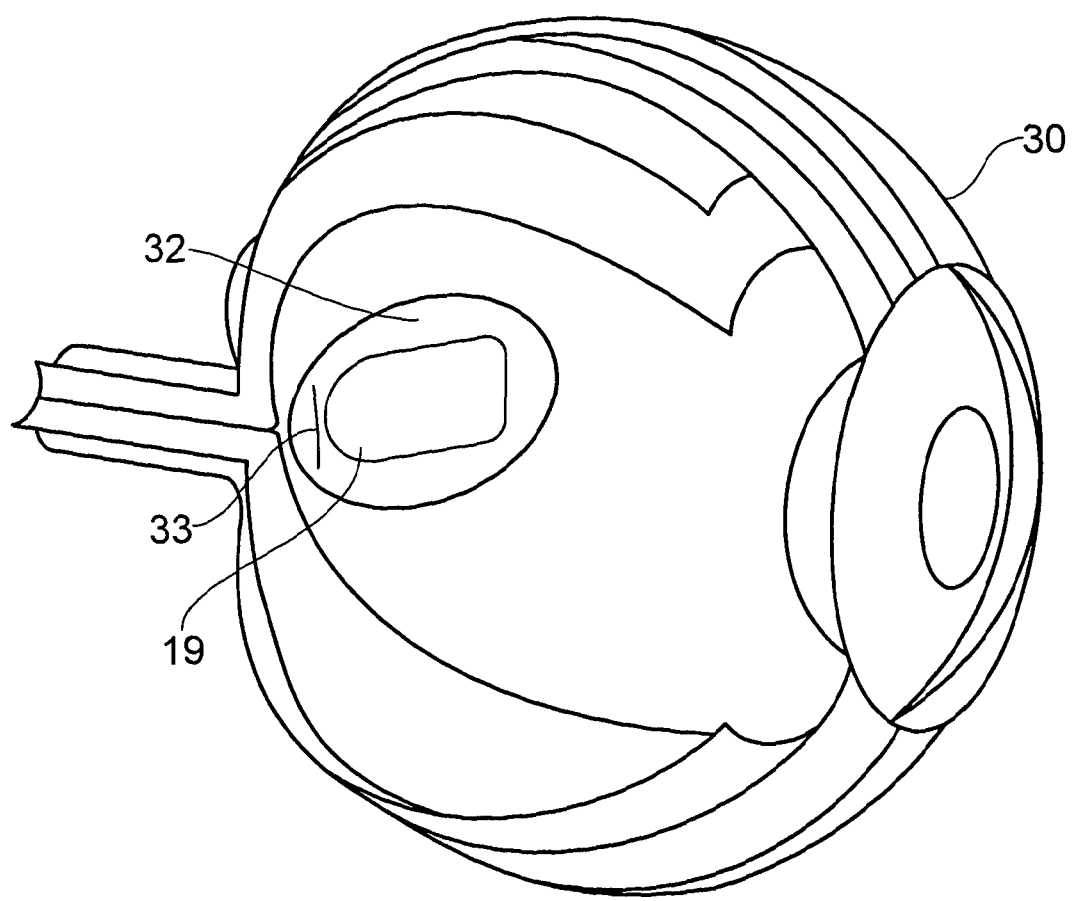
FIG. 13 is a diagram of the interior of an eye with the implant being inserted into the back of the eye.

FIG. 13 is a cut-away diagram of an interior of an eye. According to a procedure for deploying the implant, a blister 32 may be formed in or near the retina of the eye 30. An incision can then be surgically made into the blister 32 so that the implant 19 can be delivered under the retina using the device 10, which has been introduced into the eye via the slit 31.

In more detail, the procedure may follow the following steps.
1. The pupil of the eye to undergo the implantation procedure is dilated with cyclopentolate 1% and phenylephrine 2.5%;
2. Peri-orbital skin is cleaned and a sterile drape applied to cover peri-orbital and adjacent skin but to allow access to the surgical field.
3. HPMC 2% in balanced salt solution is applied to the surface of the eye periodically throughout the surgery to prevent the eye surface drying up.
4. Lateral canthotomy is performed after lateral canthus clamping
5. Eyelids are retracted
6. Localised peritomies and 3 sclerostomies are performed 2 mm from the limbus
7. A three port pars vitrectomy (Alcon, Ref. 8065741008) is performed using an indirect wide-angle viewing system
8. Posterior vitreous detachment is induced up to the major retinal vessels
9. Further vitrectomy continued.
10. 360° laser and cryo surgery performed. Use of equipment is recorded on Laser/Cryo form
11. Localised retinal bleb detachment (4×6 mm) is achieved at the vessel free region, superonasal to the disc, by sub-retinal injection of balanced salt solution (Moorfields) sodium lactate.
12. The retinotomy is enlarged using a microvitreoretinal (MVR) blade and vertical scissors.
13. The sclerostomy for patch delivery is enlarged using MVR and feather blade while the patch is prepared.
14. The infusion line is left open while the patch is inserted through the sclerostomy
15. The graft is engaged at the retinotomy and advanced into the sub-retinal space.
16. The retina is re-attached under air using back flush
17. The retinotomy is lasered and recorded. Search at periphery and laser or cryo to tears and record.
18. The air-to-silicone oil exchange
19. Sclerostomies are closed using polyglactin sutures, 6/0 Vicryl to delivery sclerostomies and 7/0 Vicryl to others
20. Intravitreal Triaminolone Acetonide 1 ml (40 mg/ml) is delivered by injection around the eye (in the subtenon space)
21. Chloamphenicol 0.5% and atropine sulphaste 1% is applied topically to the eye
22. Betamethasone 0.1% is applied to the conjunctival sac
23. 1 ml Triamcinolone Acetonide 40 mg/ml is delivered by injection around the eye (in the subtenon space) at the end of surgery.

The invention claimed is:

1. A sub-retinal, flexible implant-deploying device, said device comprising:
 a distal end having a distal tip; and
 a proximal end, wherein:
 said distal end comprises an opening to accept an inserted flexible implant and constructed and arranged to cause said flexible implant to be flexed into a curved configuration forming a flexed implant when in a carried position, and to deploy the flexed implant from said opening into a sub-retinal space;

a longitudinal axis of said proximal end and a longitudinal axis of said distal end form an angle of between 200 and 700;

said proximal end comprises an actuator connected to a flexible urging member that, when actuated, causes said flexible urging member to urge said flexed implant from said carried position to a deployed position via the distal end;

said actuator is a wheel rotatable toward or away from the distal tip, wherein rotational movement of said actuator causes linear movement of said implant; and a proximal end of said flexible urging member is secured to the wheel, and wherein rotational movement of said wheel winds or unwinds flexible urging member around said wheel.

2. A device according to claim 1, wherein said distal end comprises a longitudinal axis and walls curved in a plane perpendicular to the longitudinal axis of the distal end, said walls defining the opening at the distal end.

3. A device according to claim 2, wherein said opening is angled away from a plane perpendicular to a direction of insertion and/or deployment of the flexible implant.

4. A device according to claim 2, wherein said walls curved in a plane perpendicular to the longitudinal axis of the distal end cause said flexible implant to curve in a direction generally transverse to the direction in which said flexed implant is deployed.

5. A device according to claim 2, wherein, when said implant is in said carried position or when said implant is urged from said carried position to a deployed position, said walls restrict movement of said implant in a direction generally transverse to the direction in which said implant is deployed.

6. A device according to claim 2, wherein said walls are arranged to guide said implant as it moves from said carried position to a deployed position, or vice versa.

7. A device according to claim 1, wherein the angle is between 30° and 50°.

8. A device according to claim 1 wherein said urging member is a wire.

9. A device according to claim 8 wherein said urging member is a coiled wire.

10. A device according to claim 1, wherein said distal end comprises a guiding means arranged to guide said urging member.

11. A device according to claim 10, wherein said guiding means is a groove extending along at least a portion of an interior wall of the distal end of the device.

12. A device according to claim 1, wherein the distal tip is removably attachable to the proximal end.

13. A device according to claim 1, wherein the proximal end comprises a handle.

14. A combination of:
    an implant wherein the implant is flexible, substantially planar, substantially flat and comprises stem cells, a drug, or radioactive material; and
    a device according to claim 1;
wherein the implant is inserted into the device, thereby forming a flexed implant.

15. The device according to claim 1 wherein the angle is between 40° and 50°.

16. The device according to claim 1 wherein the angle is between 30° and 50°.

17. A combination of:
    an implant wherein the implant is flexible, substantially planar, substantially flat; and
    a device according to claim 1;
wherein the implant is inserted into the device, thereby forming a flexed implant.

* * * * *